(12) United States Patent
Gabazza et al.

(10) Patent No.: US 9,894,889 B2
(45) Date of Patent: Feb. 20, 2018

(54) TRANSGENIC NON-HUMAN MAMMAL THAT EXPRESSES HUMAN MMP2

(71) Applicant: MIE UNIVERSITY, Tsu-shi (JP)

(72) Inventors: Esteban C. Gabazza, Tsu (JP); Osamu Taguchi, Tsu (JP); Tetsu Kobayashi, Tsu (JP)

(73) Assignee: MIE UNIVERSITY, Tsu-Shi (JP)

( * ) Notice: Subject to any disclaimer, the term of this patent is extended or adjusted under 35 U.S.C. 154(b) by 0 days.

(21) Appl. No.: 15/103,457

(22) PCT Filed: Dec. 10, 2014

(86) PCT No.: PCT/JP2014/082691
§ 371 (c)(1),
(2) Date: Sep. 14, 2016

(87) PCT Pub. No.: WO2015/087916
PCT Pub. Date: Jun. 18, 2015

(65) Prior Publication Data
US 2016/0374319 A1 Dec. 29, 2016

(30) Foreign Application Priority Data
Dec. 12, 2013 (JP) .................... 2013-256900

(51) Int. Cl.
*A01K 67/027* (2006.01)
*A01K 67/02* (2006.01)
*C12N 15/873* (2010.01)
*C12N 15/90* (2006.01)
*C12N 9/64* (2006.01)
*C12N 15/85* (2006.01)
*C12N 15/09* (2006.01)

(52) U.S. Cl.
CPC ........ *A01K 67/0278* (2013.01); *A01K 67/027* (2013.01); *C12N 9/6416* (2013.01); *C12N 9/6491* (2013.01); *C12N 15/8509* (2013.01); *C12Y 304/24024* (2013.01); *A01K 2217/052* (2013.01); *A01K 2227/105* (2013.01); *A01K 2267/035* (2013.01); *A01K 2267/0368* (2013.01); *C12N 15/09* (2013.01); *C12N 2015/8527* (2013.01); *C12N 2830/15* (2013.01)

(58) Field of Classification Search
CPC ............. A01K 67/0278; A01K 67/027; A01K 2217/052; A01K 2227/105; A01K 2267/035; A01K 2267/0368; C12N 15/09; C12N 15/8509
USPC ................ 800/18, 9, 25; 435/455, 320.1
See application file for complete search history.

(56) References Cited

U.S. PATENT DOCUMENTS

| 5,858,355 A | 1/1999 | Glorioso et al. |
| 7,642,402 B2 | 1/2010 | Hachiya et al. |
| 2007/0143866 A1 | 6/2007 | Hachiya et al. |

FOREIGN PATENT DOCUMENTS

| JP | H08511507 A | 12/1996 |
| JP | 2007167060 A | 7/2007 |

OTHER PUBLICATIONS

Mullins et al. (1996) J. Clin. Invest., vol. 98(11), pp. S37-S40.*
Dahi et al. (2011) Int. J. Exp. Path., vol. 92, 50-56.*
Bergman, M. R. et al., Cardiac matrix metalloproteinase-2 expression independently induces marked ventricular remodeling and systolic dysfunction, American Journal of Physiology Heart and Circulatory Physiology, 2006, vol. 292, pp. H1847-H1860.
Cheng, S., et al., Matrix metalloproteinase 2 and basement membrane integrity: a unifying mechanism for progressive renal injury, The FASEB Journal, 2006, vol. 20, p. E1248-E1256 (Full Length Article).
D' Armiento J, et al., Collagenase Expression in the Lungs of Transgenic Mice Causes Pulmonary Emphysema, Cell, 1992, vol. 71 (6), pp. 955-961.
Dahi, S., et al., Transgenic expression of matrix metalloproteinase-2 induces coronary artery ectasia, International Journal of Experimental Pathology, 2011, vol. 92, pp. 50-56.
English translation of International Search Report for parent application No. PCT/JP2014/082691 dated Mar. 17, 2015.
Zhou, H. Z. et al., Transgenic MMP-2 expression induces latent cardiac mitochondrial dysfunction, Biochemical and Biophysical Research Communications, 2007, vol. 358(1), pp. 189-195.
English translation of International Preliminary Report on Patentability for parent application No. PCT/JP2014/082691 dated May 4, 2016.
Cheng, S., et al., Matrix metalloproteinase 2 and basement membrane integrity: a unifying mechanism for progressive renal injury, The FASEB Journal, 2006, vol. 20, pp. 1898-1890 (FJ Express Summary).
Written Opinion for parent application No. PCT/JP2014/082691 dated Mar. 17, 2015 with machine translation of Box. No. V, Section 2, Rejections 1 and 2.

* cited by examiner

*Primary Examiner* — Anne Marie S Wehbe
(74) *Attorney, Agent, or Firm* — J-Tek Law PLLC; Jeffrey D. Tekanic; Scott T. Wakeman

(57) ABSTRACT

A transgenic non-human mammal has a genome that includes an early-immediate enhancer of human cytomegalovirus (CMV enhancer), a β-actin promoter and the entire gene region of human matrix metalloproteinase 2 (hMMP2) disposed downstream of the promoter. The hMMP2 is systemically expressed in the transgenic non-human mammal, which thus provides a suitable animal model for studying chronic obstructive pulmonary disease and related diseases and conditions.

7 Claims, 19 Drawing Sheets

(1) DraI
5093 bp
1504 bp
692 bp
19 bp (2) EcoRI
5201 bp
2107 bp (3) HindIII
7308 bp (4) NcoI
4405 bp
1394 bp
843 bp
381 bp
285 bp (5) SacI
3965 bp
3127 bp
216 bp (6) SpeI
7308 bp

TRANSGENIC NON-HUMAN MAMMAL THAT EXPRESSES HUMAN MMP2

CROSS-REFERENCE

This application is the US national stage of International Patent Application No. PCT/JP2014/082691 filed on Dec. 10, 2014, which claims priority to Japanese Patent Application No. 2013-256900 filed on Dec. 12, 2013.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| MIE004_Seq_List.txt | Jun. 16, 2016 | 2 |

TECHNICAL FIELD

The present invention relates to transgenic (TG) non-human mammals that express human MMP2 (metalloproteinase 2; hereinafter referred to as "hMMP2").

BACKGROUND ART

Matrix metalloproteinases (MMP) are a group of metalloproteinases and it is a generic term for proteinases that include a metal ion in its active center. More than 20 types of MMPs are known, such as MMP1, MMP2, MMP3, MMP7, MMP8, MMP9, and MMP10. MMPs exhibit functions such as degradation of extracellular matrix including collagen, proteoglycan, elastin, etc., degradation of proteins expressed on cell surfaces, and processing of physiologically-active substances. There is a report of a transgenic (TG) non-human mammal (mouse) that expresses human MMP1 (hMMP1) (Non-Patent Document 1). Although this TG mouse expressed hMMP1 in lung tissue, expression in organs of the entire body was not observed. In addition, TG non-human mammals that systemically express hMMP2 are not known.

Concurrently, chronic obstructive pulmonary disease (COPD) is a general term that consolidates the disease concept that has been pathologically referred to as emphysema and the disease concept that has been clinically referred to as chronic bronchitis. These concepts were specified in an international guideline (GOLD) in 2001 and in clinical practice guidelines of the Japanese Respiratory Society. In addition, these disease concepts have been formalized at the levels of Japanese and international academic societies. As one of the COPDs, emphysema is a disease associated with destructive changes in the alveolar walls, and exhibits a condition in which aerated sections ranging from the respiratory tract and the terminal bronchiole to the periphery are abnormally enlarged. Although the progression of COPD is slow, COPD further progresses to cor pulmonale if left untreated. COPD is a disease that develops after a history of smoking for 20 years or more. In Japan, the number of deaths due to COPD in 2011 was 16,639, and continues to increase.

PRIOR ART DOCUMENT

Non-Patent Document

Non-Patent Document 1: D'Armiento J, Dalal S S, Okada Y, Berg R A, Chada K., Collagenase expression in the lungs of transgenic mice causes pulmonary emphysema, Cell. 1992 Dec. 11; (6): 955-61.

SUMMARY OF THE INVENTION

Although systemic expression of hMMP2 in the entire body is required to understand the function of hMMP2 in the entire body, such a TG non-human mammal has not been developed thus far.

In addition, it has been desired in the art to develop a suitable animal model for studying COPD treatment and preventive methods. Although some research and development have been conducted, a satisfactory animal model has not yet been developed.

The present invention was made in view of the circumstances described above, and its objective is to provide TG non-human mammals that express hMMP2 in tissues of the entire body and to provide an animal model for COPD and other disease models.

To accomplish the above-mentioned objectives, an hMMP2-expressing TG non-human mammal of the present teachings preferably includes a promoter for gene expression and the entire gene region of hMMP2 that is disposed downstream of the promoter and whose expression is induced systemically.

Possible promoters include, e.g., a CAG promoter, β-actin promoter, hTERT promoter, PSA promoter, c-myc promoter, GLUT promoter, OCT3/4 promoter, NANOG promoter, Nestin promoter, HSP70 promoter, HSP90 promoter, p53 promoter, albumin promoter, TNF-alpha promoter, SV40 promoter, EF1-α promoter, CMV-i promoter and CMV promoter, etc. When a β-actin promoter is used, its species of origin is not limited, and a promoter derived, e.g., from a human or chicken can be used.

In the present teachings, non-human mammals may include mice, rats, rabbits, dogs, pigs, goats, sheep, horses, cattle, monkeys, etc.; among them, mice are preferable in terms of ease of handling. Furthermore, in the case of mice, the strain C57BL/6J is preferable.

Additionally, in order to increase the expression level of hMMP2, preferably an enhancer is disposed upstream of the promoter region. Possible enhancers include, e.g., a CMV enhancer, SV40 enhancer, hTERT enhancer, etc. For the enhancer, either only one enhancer or a plurality of the same or different enhancers can be used. In the alternative, a combination of a plurality of different enhancers can be used. When using a plurality of different enhancers, their order is not limited. For example, a hTERT enhancer, SV40 enhancer and CMV enhancer linked in this order can be given as an example.

It is noted that, when the expression level of the hMMP2 is excessively high, the average lifespan of the TG non-human mammals is likely to become significantly shortened, and thus an excessive expression should be appropriately controlled (avoided).

A method for producing an hMMP2-expressing TG non-human mammal according to another aspect of the present teachings preferably includes preparing an hMMP2 expression construct by incorporating, in an expressible state, the entire gene region of the human matrix metalloproteinase 2 (hMMP2) downstream of a promoter for gene expression;

this hMMP2 expression construct is introduced (microinjected) into a fertilized egg that is then implanted in a non-human mammal and allowed to gestate until delivery.

In this aspect of the present teachings, it is preferable that, after the non-human mammal is allowed to deliver, each offspring is raised as a founder candidate individual, genomic DNA is extracted from tissues of each founder candidate individual, and then the presence of the hMMP2 expression construct is confirmed to obtain a founder individual in which the presence of the hMMP2 expression construct could be confirmed.

In addition, as the promoter for gene expression, a CAG promoter or a β-actin promoter is preferable. Furthermore, as the non-human mammal, a mouse is preferable.

A TG non-human mammal obtained according to the present teachings preferably has the characteristic that it naturally develops chronic obstructive pulmonary disease (COPD), such as emphysema, extrapulmonary lesions (renal failure, liver failure, encapsulating peritoneal sclerosis), etc. By administering an inducer, it is capable of developing chronic obstructive pulmonary disease (COPD), extrapulmonary lesions (renal failure, liver failure, encapsulating peritoneal sclerosis), etc. more quickly and can develop pulmonary fibrosis, airway remodeling, pulmonary hypertension, etc. It is noted that decreased muscle mass, osteoporosis, anemia and cardiovascular lesions are known to develop with worsening COPD. TG non-human mammals of the present teachings can also develop these disease models. As the inducer, cigarette (tobacco) smoke, a cigarette (tobacco) smoke extract or a cigarette component (a component of tobacco) as well as other substances including albumin, bleomycin, environmental pollutants, proteases, etc., can be given as examples. In addition, as the administration method thereof, inhalation, intravenous injection, oral administration, intraperitoneal administration, subcutaneous administration, transtracheal administration, etc., can be given as examples.

According to the present teachings, a TG non-human mammal can be provided that systemically expresses hMMP2, naturally develops COPD and extrapulmonary lesions on a long-term basis, by administering cigarette smoke extracts, etc., develops COPD and extrapulmonary lesions in a short period of time, and develops pulmonary fibrosis, airway remodeling and pulmonary hypertension. Herein, "long-term basis" means about 8 to 12 months, and "short period of time" means about 2 to 4 weeks. Research on COPD and other diseases can be dramatically advanced by using such an hMMP2-expressing TG non-human mammal.

BRIEF DESCRIPTION OF THE FIGURES

FIG. 5(A) is a photograph showing the CAG-hMMP2 expression construct digested by HindIII+SpeI and electrophoresis migration in a 1% agarose gel, (B) is a photograph showing the electrophoresis migration of the HindIII+SpeI fragment of the CAG-hMMP2 expression construct in a 0.8% agarose gel, and (C) is a photograph showing the electrophoresis migration of the CAG-hMMP2 that was cut out and separated from the agarose gel for purification using an 1% agarose gel.

FIG. 11(A) is a cross-section image in a direction perpendicular to the backbone, and (B) is a cross-section image along the direction of the backbone (The same applies to FIG. 12).

FIG. 18(A) is a graph that shows the total cell number in BALF, (B) is a graph that shows the total protein concentration in BALF, (C) is a graph that shows the MCP-1/GAPDH ratio in lung tissue; (D) is a lung microphotograph of an hMMP2-expressing TG mouse treated with saline and (E) is a lung microphotograph of a hMMP2-expressing TG mouse treated with bleomycin.

FIG. 19(A) is a graph that shows the total cell number in BALF, (B) is a graph that shows the IL5/GAPDH ratio in the lung tissue, (C) is a graph that shows IL-4 mRNA expression in lung tissue, (D) is a graph that shows the IL-13/GAPDH ratio in lung tissue, (E) is a lung microphotograph of an hMMP2-expressing TG mouse after saline inhalation, and (F) is a lung microphotograph of a hMMP2-expressing TG mouse after ovalbumin inhalation.

DETAILED DESCRIPTION

Next, embodiments of the present teachings will be explained with reference to the figures and tables, but the technical scope of the present invention is not limited by these embodiments and can be carried out in various forms without changing the gist of the invention.

<Preparation of hMMP2-Expressing TG Mice>

1. Construction of hMMP2 Expression Vector

Figure 1:
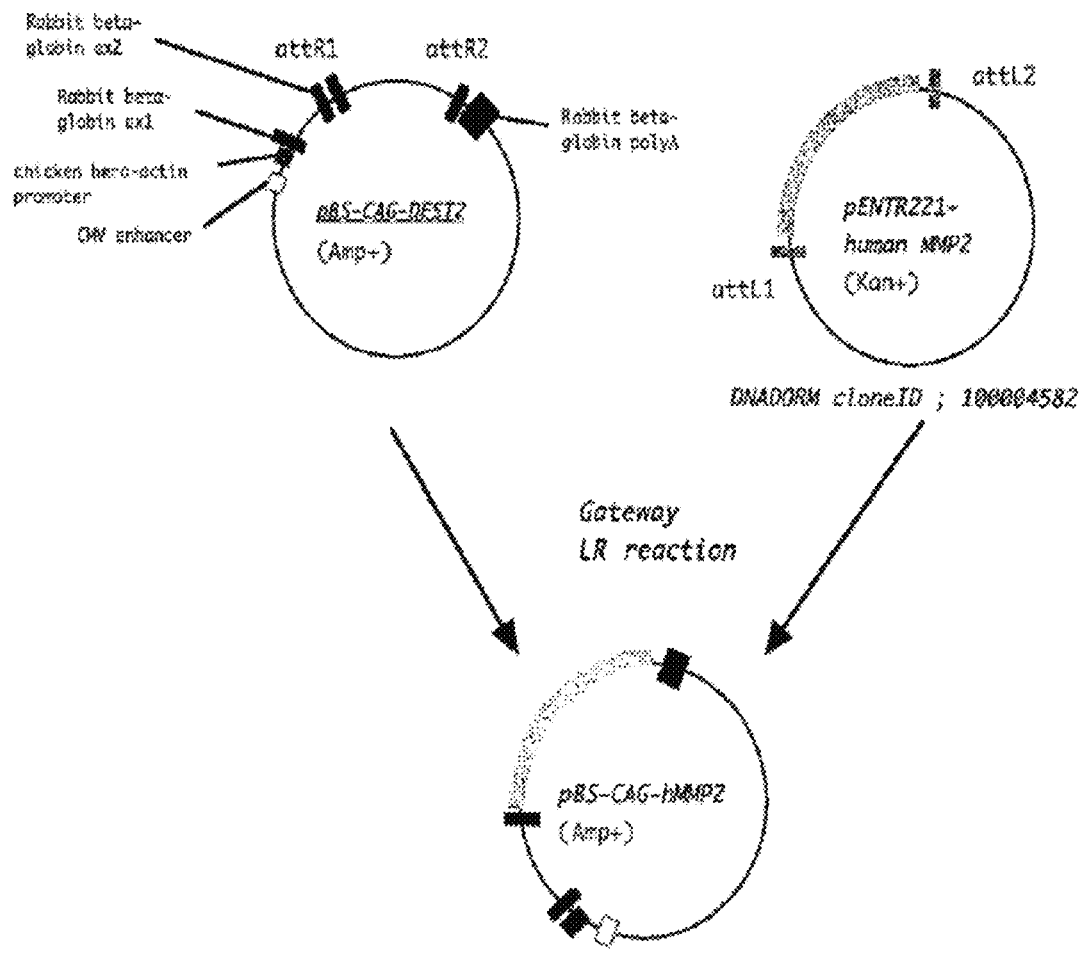
FIG. 1 illustrates a strategy for preparation of an hMMP2 expression construct (expression vector).
Figure 2:
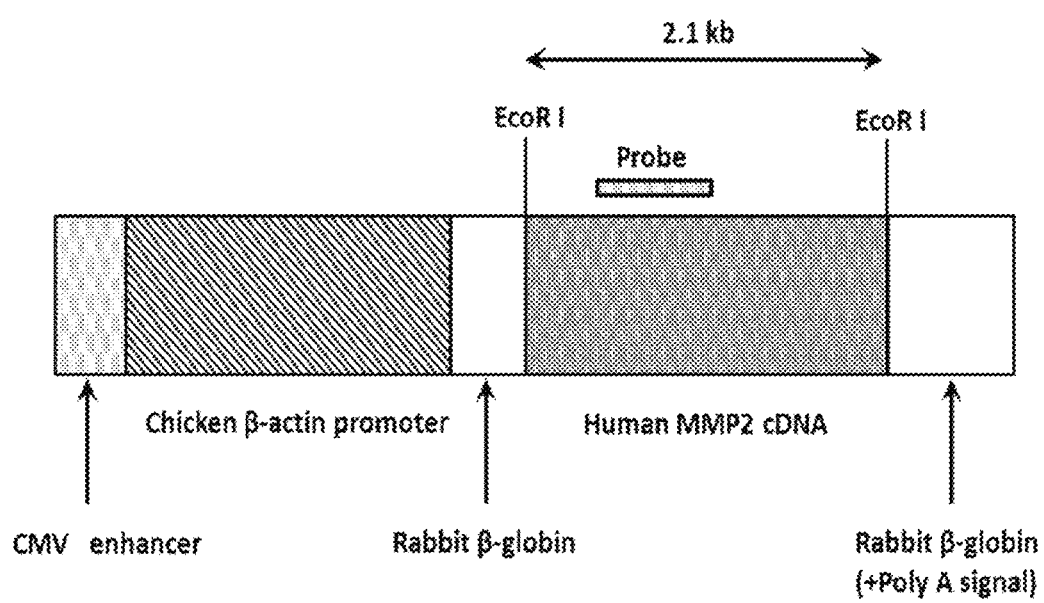
FIG. 2 shows a map of the hMMP2 expression construct.

As shown in FIG. 1, an hMMP2 expression vector pBS-CAG-hMMP2 was constructed by subcloning an hMMP2 cDNA fragment into a pBS-CAG-DESTZ vector, from a pENTR vector (pENTR221-human MMP2) into which the hMMP2 cDNA (accession number: BC002576) was cloned, by using the Gateway® LR reaction (Invitrogen®) (FIG. 1 and FIG. 2). The hMMP2 expression construct was configured so as to have only one EcoRI site for genetic analysis of TG mice.

Expression of the hMMP2 cDNA was carried out by using an early-immediate enhancer of human cytomegalovirus (CMV enhancer), followed by a chicken β actin in which a promoter, a first exon and an intron of the chicken β actin were linked (chicken β-actin promoter). A transcript of hMMP2 having a stop codon and a poly (A) signal was linked upstream of a poly (A) sequence (poly A signal) of a rabbit β-globin (FIG. 2). Although hMMP2 has been identified as "human MMP2" and "Human MMP2" in FIG. 1 and FIG. 2, respectively, these two terms designate the same thing.

An mRNA transcript of the transgene is constructed as a part of a first exon of the chicken β-actin (which is transcribed but not translated); the mRNA is transcribed to the hMMP2 cDNA.

Figure 3:
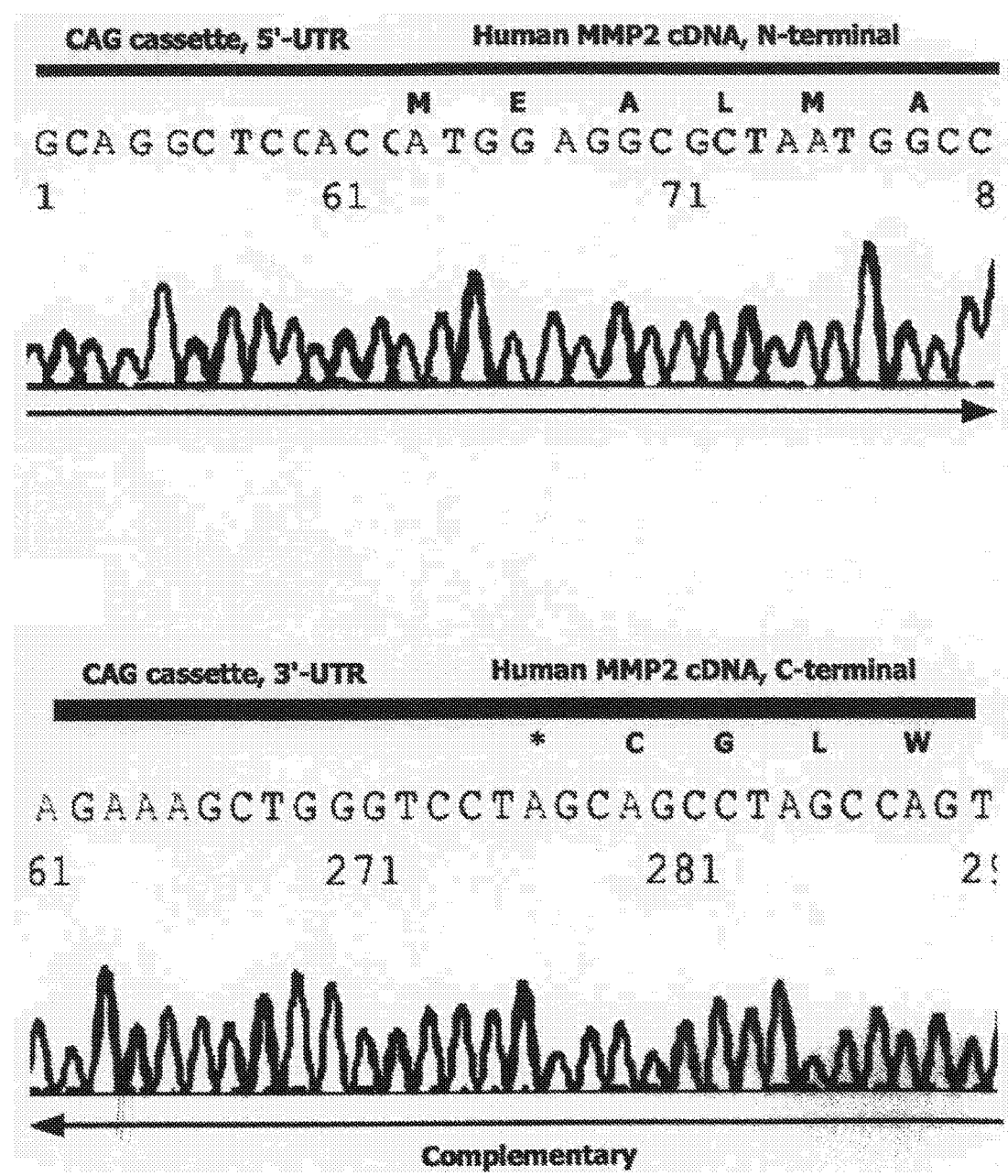
FIG. 3 illustrates the confirmation of the base sequences of the CAG expression construct and the hMMP2 cDNA.
Figure 4:
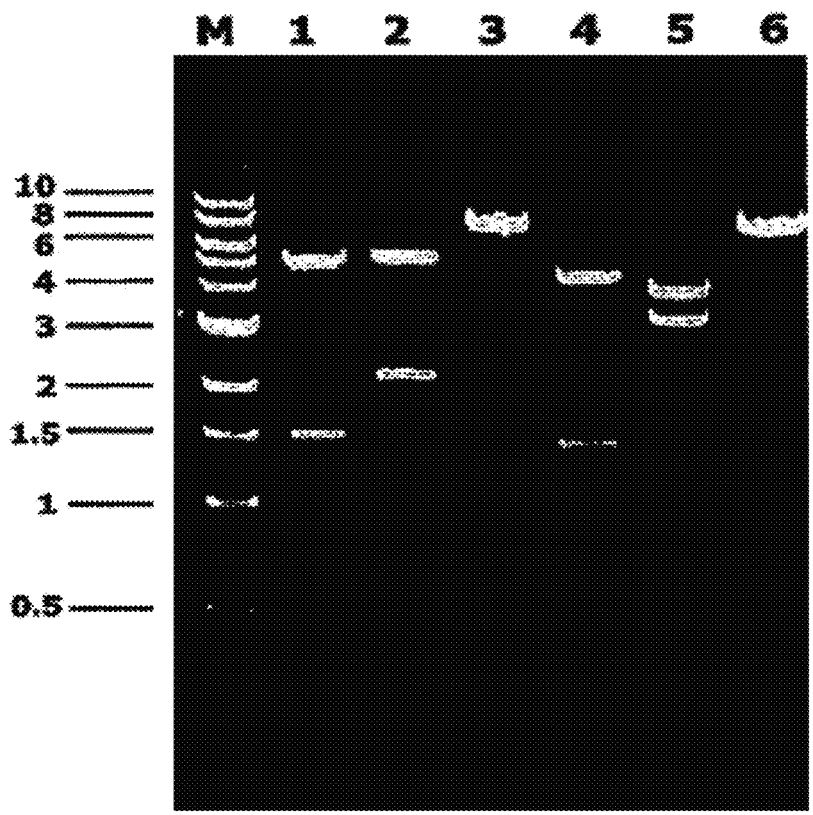
FIG. 4 is a gel photograph that shows fragments of the hMMP2 expression construct after digestion by various restriction enzymes and then electrophoresis.

After the hMMP2 expression construct was prepared, the DNA sequence of the portion bound to the hMMP2 cDNA was confirmed by restriction enzyme mapping and sequence analysis. As a result, it was confirmed that the hMMP2 cDNA had been cloned into a CAG expression vector as planned (FIG. 3). In addition, sizes of fragments made by restriction enzymes DraI, EcoRI, HindIII, NcoI, SacI, SpeI were consistent with the expected fragment sizes (FIG. 4).

With the above results, preparation of the hMMP2 expression construct was completed.

2. Purification of a Linear DNA for Producing TG Mice

After the expression vector pBS-CAG-hMMP2 of the hMMP2 was introduced into DH5α competent cells (Invitrogen®), the cells were seeded on an LB agar medium containing ampicillin, and an ampicillin-resistant strain was selected. A single colony of the ampicillin-resistant strain was picked up (extracted), and then cultured in a liquid medium while shaking for a whole day and night.

Figure 5:
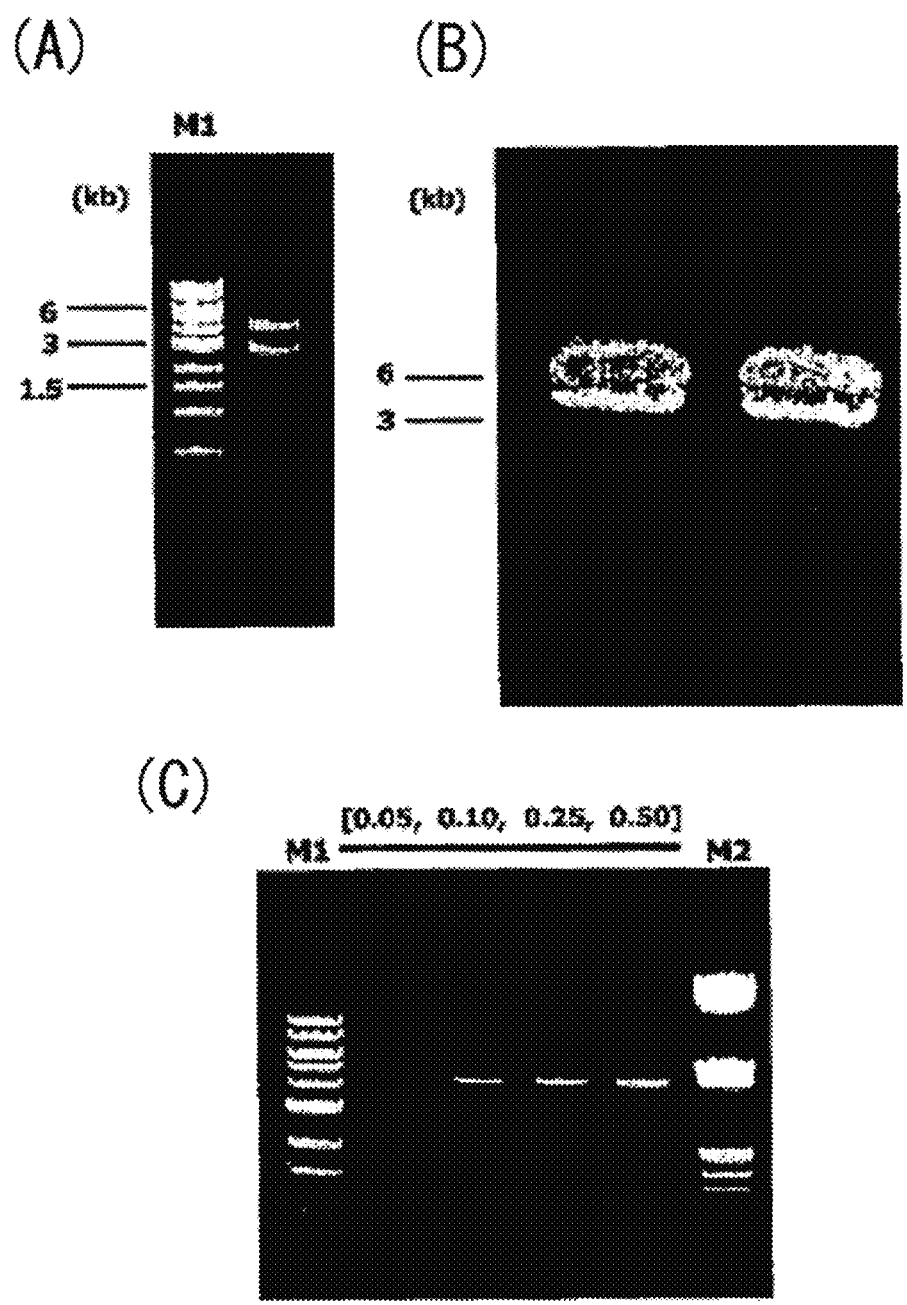
FIG. 5 shows gel photographs of the results of purification of the CAG-hMMP2 expression construct.

The cloned pBS-CAG-hMMP2 was purified by using a plasmid extraction kit (PlasmidMidi Kit, QIAGEN®), to which the restriction enzymes HindIII+SpeI were added, and incubated at 37° C. for 16 hours. Production of a DNA fragment derived from the vector and a DNA fragment for hMMP2 expression was confirmed by 1% agarose gel electrophoresis (FIG. 5(A)). Subsequently, the DNA fragments were collected by phenol/chloroform extraction and isopropanol precipitation.

The collected DNA fragments were redissolved in TE, electrophoresed in a 0.8% agarose gel, and then a DNA fragment for hMMP2 expression was excised from the separated DNA fragments. The excised DNA fragment was purified by using a DNA extraction kit (DNA Gel Extraction Kit, QIAGEN®), its purity was confirmed by 1% agarose gel electrophoresis, and its concentration was determined by using a NanoDrop® spectrophotometer (AGC TECHNO GLASS Co., Ltd.). The DNA fragment was diluted so that its concentration was 2 ng/μL to obtain a DNA solution of hMMP2 (CAG-hMMP2 expression construct) for microinjection. This solution was stored at −25° C. until use in the test.

3. Microinjection of the Expression Construct into Fertilized Eggs

Fertilized eggs were collected from female mice which had been subjected to superovulation induction by administering PMSG and hCG, and the CAG-hMMP2 expression construct was introduced into the eggs by using a microinjection method. The fertilized eggs, into which the CAG-hMMP2 expression construct had been introduced, were implanted into the fallopian tube of pseudopregnant mice.

From C57BL/6J female mice that were mated after the superovulation induction, 862 fertilized eggs were collected. From among them, 266 fertilized eggs were injected with the CAG-hMMP2 expression construct. When the fertilized eggs after injection were observed under a microscope, 236 of the fertilized eggs were still in a stable state after the microinjection. From among them, 210 of the fertilized eggs could be implanted into the pseudopregnant mice.

4. Raising of hMMP2-Expressing TG Mice and Confirmation of Founder Individuals (1) Raising of hMMP2-Expressing TG Mice Offspring obtained by natural birth from fertilized eggs of C57BL/6J mice microinjected with the CAG-hMMP2 expression construct were raised until weaning. The hMMP2 TG mouse founder candidate individuals were weaned at 3 weeks old, given ear tags for fixed identifications, and then their tail tissues were subjected to biopsy and stored at −80° C. until analysis.

210 fertilized eggs had been implanted. After an approximately 3-week pregnancy period, 65 mouse offspring could be obtained from surrogate mice into which the fertilized eggs injected with the CAG-hMMP2 expression construct had been implanted. The surrogate mice, from which these offspring were born, raised their offspring, and as a result all of 65 individuals could be raised until weaning. Tail tissue samples were collected from all of these weaned individuals as well as from some individuals who died after weaning.

The number of offspring from the initial embryos into which the expression construct had been introduced and the number of weaned individuals were satisfactory. Consequently, it was considered that there was no adverse effect on the development and differentiation of the fertilized eggs due to the injection of the expression construct.

(2) Genotyping of Founder Individuals of hMMP2 Expression TG Mice

The tail tissue of the candidate individuals of the hMMP2 TG mice, which tail tissue had been stored at −80° C., was thawed at room temperature, a lysis buffer solution containing 1% of SDS (Wako® Pure Chemical Industries, Ltd.), 1 mg/mL of Actinase E (Kaken Pharmaceutical Co., Ltd.) and 0.15 mg/mL of Protease K (Merck® KGaA) was added, and it was shaken at 55° C. for 16 hours to solubilize the tissue. Proteins that bound to the solubilized genomic DNA were removed from the tissue by phenol extraction and phenol/chloroform extraction. After RNA contained in the genomic DNA was degraded by RNaseA (Sigma®), high molecular weight genomic DNA was precipitated by isopropanol precipitation. The genomic DNA was washed with 70% ethanol and air-dried, and then redissolved in 50 µL of TE.

The DNA concentration of the genomic DNA solution prepared from each sample was determined by spectrophotometry, and the volume of the genomic DNA solution that corresponded to 5 µg of DNA was determined from the DNA concentration value of each sample.

The CAG-hMMP2 expression construct used for microinjection was diluted so as to provide 1, 3, 10 or 30 copies, 5 µg of a separately prepared genomic DNA of a control mouse was added and positive control DNA for Southern blotting was prepared. On the other hand, 5 µg of genomic DNA of the control mouse was used as a negative control DNA for Southern blotting.

The genomic DNA concentration, which was prepared by extraction from the tissue of the hMMP2 TG mouse founder candidate individuals that were raised to weaning, was a sufficient recovered amount for Southern analysis using 5 µg of DNA (Table 1).

TABLE 1

| Sample No. | ID | Sex | Date of Birth | Genomic DNA conc. (ng/µl) |
|---|---|---|---|---|
| 1 | 1_1 | ♂ | Oct. 12, 2020 | 473 |
| 2 | 1_2 | ♂ | Oct. 12, 2020 | 664 |
| 3 | 1_3 | ♂ | Oct. 12, 2020 | 280 |
| 4 | 1_4 | ♂ | Oct. 12, 2020 | 443 |
| 5 | 1_5 | ♂ | Oct. 12, 2020 | 749 |
| 6 | 1_6 | ♂ | Oct. 12, 2020 | 182 |
| 7 | 1_7 | ♂ | Oct. 12, 2020 | 669 |
| 8 | 1_8 | ♂ | Oct. 12, 2020 | 720 |
| 9 | 1_9 | ♂ | Oct. 12, 2020 | 780 |
| 10 | 1_10 | ♂ | Oct. 12, 2020 | 504 |
| 11 | 2_1 | ♂ | Oct. 12, 2020 | 484 |
| 12 | 2_2 | ♂ | Oct. 12, 2020 | 568 |
| 13 | 2_3 | ♂ | Oct. 12, 2020 | 574 |
| 14 | 2_4 | ♂ | Oct. 12, 2020 | 556 |
| 15 | 2_5 | ♂ | Oct. 12, 2020 | 663 |
| 16 | 2_6 | ♂ | Oct. 12, 2020 | 914 |
| 17 | 2_7 | ♂ | Oct. 12, 2020 | 483 |
| 18 | 2_8 | ♂ | Oct. 12, 2020 | 836 |
| 19 | 2_9 | ♂ | Oct. 12, 2020 | 777 |
| 20 | 2_20 | ♂ | Oct. 12, 2020 | 845 |
| 21 | 3_1 | ♂ | Oct. 12, 2020 | 737 |
| 22 | 3_2 | ♂ | Oct. 12, 2020 | 418 |
| 23 | 3_3 | ♂ | Oct. 12, 2020 | 929 |
| 24 | 3_4 | ♂ | Oct. 12, 2020 | 913 |
| 25 | 3_5 | ♂ | Oct. 12, 2020 | 735 |
| 26 | 3_6 | ♂ | Oct. 12, 2020 | 478 |
| 27 | 3_7 | ♂ | Oct. 12, 2020 | 613 |
| 28 | 3_8 | ♂ | Oct. 12, 2020 | 1021 |
| 29 | 3_9 | ♂ | Oct. 12, 2020 | 761 |
| 30 | 3_30 | ♂ | Oct. 12, 2020 | 632 |
| 31 | 4_1 | ♀ | Oct. 12, 2020 | 741 |
| 32 | 4_2 | ♀ | Oct. 12, 2020 | 774 |
| 33 | 4_3 | ♀ | Oct. 12, 2020 | 845 |
| 34 | 4_4 | ♀ | Oct. 12, 2020 | 1042 |
| 35 | 4_5 | ♀ | Oct. 12, 2020 | 946 |
| 36 | 4_6 | ♀ | Oct. 12, 2020 | 843 |
| 37 | 4_7 | ♀ | Oct. 12, 2020 | 605 |
| 38 | 4_8 | ♀ | Oct. 12, 2020 | 592 |
| 39 | 4_9 | ♀ | Oct. 12, 2020 | 1013 |
| 40 | 4_40 | ♀ | Oct. 12, 2020 | 403 |
| 41 | 5_1 | ♀ | Oct. 12, 2020 | 573 |
| 42 | 5_2 | ♀ | Oct. 12, 2020 | 851 |
| 43 | 5_3 | ♀ | Oct. 12, 2020 | 841 |
| 44 | 5_4 | ♀ | Oct. 12, 2020 | 783 |
| 45 | 5_5 | ♀ | Oct. 12, 2020 | 545 |
| 46 | 5_6 | ♀ | Oct. 12, 2020 | 893 |
| 47 | 5_7 | ♀ | Oct. 12, 2020 | 970 |
| 48 | 5_8 | ♀ | Oct. 12, 2020 | 902 |
| 49 | 5_9 | ♀ | Oct. 12, 2020 | 403 |
| 50 | 5_50 | ♀ | Oct. 12, 2020 | 700 |
| 51 | 6_1 | ♀ | Oct. 12, 2020 | 575 |
| 52 | 6_2 | ♀ | Oct. 12, 2020 | 638 |
| 53 | 6_3 | ♀ | Oct. 12, 2020 | 671 |
| 54 | 6_4 | ♀ | Oct. 12, 2020 | 817 |
| 55 | 6_5 | ♀ | Oct. 12, 2020 | 885 |
| 56 | 6_6 | ♀ | Oct. 12, 2020 | 655 |
| 57 | 6_7 | ♀ | Oct. 12, 2020 | 984 |
| 58 | 7_1 | ♂ | Oct. 12, 2020 | 714 |
| 59 | 7_2 | ♂ | Oct. 12, 2020 | 629 |
| 60 | 7_3 | ♂ | Oct. 12, 2020 | 500 |
| 61 | 7_4 | ♂ | Oct. 12, 2020 | 640 |
| 62 | 7_5 | ♂ | Oct. 12, 2020 | 1160 |
| 63 | 7_6 | ♂ | Oct. 12, 2020 | 754 |
| 64 | 7_7 | ♂ | Oct. 12, 2020 | 606 |
| 65 | 7_8 | ♂ | Oct. 12, 2020 | 1031 |

Restriction enzyme EcoRI was added to the genomic DNA prepared from each sample, to the positive control DNA and to the negative control DNA, and incubated at 37° C. for 16 hours. The EcoRI fragments of the produced genomic DNA were precipitated by isopropanol precipitation, washed with 70% ethanol, air-dried, and then redissolved in TE. These genomic DNA fragments were electrophoresed using a 1.2% agarose gel. The genomic DNA fragments separated in the agarose gel were visualized by a UV transilluminator and photographed together with a scale.

Figure 6:
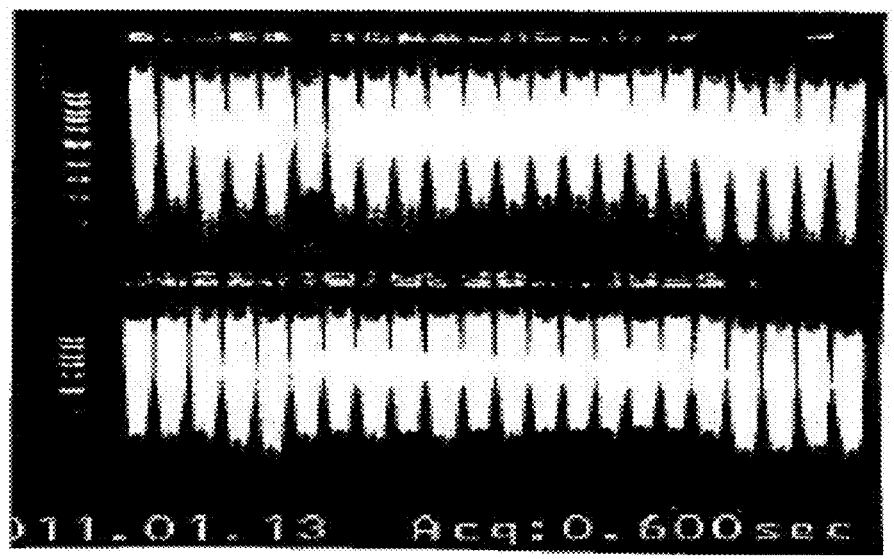
FIG. 6 shows photographs of genomic DNA extracted from the tail tissue of founder candidate individuals, a CAG-hMMP2 expression construct, a positive control containing 1, 3, 10, 30 copies and control mouse genomic DNA, as well as negative control DNA containing only the control mouse genomic DNA that were digested by the restriction enzyme EcoRI and then separated by electrophoresis in an agarose gel.
Figure 6:
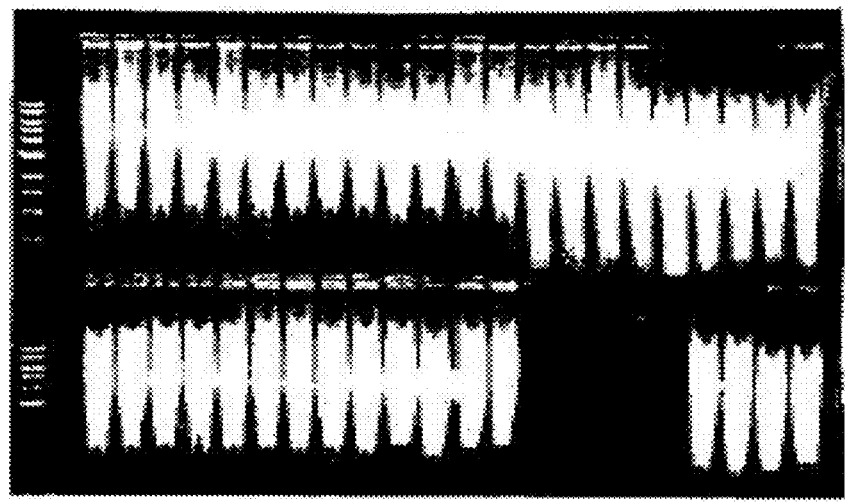

As shown in FIG. 6, high molecular weight to low molecular weight DNA fragments were observed in the agarose gel after electrophoresis, and various sizes of produced DNA fragments were observed to be uniformly separated by electrophoresis.

This agarose gel was immersed in 0.25 N hydrochloric acid, gently shaken for 10 minutes, then immersed in 0.4 N sodium hydroxide, and gently shaken again for 10 minutes. The genomic DNA fragments separated in the agarose gel were transferred to a nylon membrane (Hybond®-XL; GEH) by a capillary method using 0.4 N sodium hydroxide at room temperature for 16 hours. The nylon membrane to which the genomic DNA fragments were transferred was immersed in 2×SSC, gently shaken for 10 minutes, then air-dried, and stored at room temperature until used for the hybridization.

The hMMP2 probe 2 fragment was labeled with [$^{32}$P] using a DNA labeling kit (Megaprime® DNA Labelling System; GEH) by a random prime method. A [$^{32}$P]-labeled fragment was produced using a Sephadex® spin column (ProbeQuant® G-50 Micro Columns; GEH), and will be referred to as [$^{32}$P]-labeled hMMP2 probe 2.

The nylon membrane, onto which the genomic DNA fragments were transferred, was put in a hybridization buffer solution and preincubated at 65° C. for 1 hour. Subsequently, it was heated at 95° C. for 5 minutes, and thereafter cooled in ice for 5 minutes, to which the denatured [$^{32}$P]-labeled hMM2 probe was added, and incubated at 65° C. for 4 hours. After that, the nylon membrane was taken out, and washed with 0.1% SDS and 0.5×SSC at 65° C. for about 15 minutes. Radioactivity originating in the probe bound to the membrane was monitored with a radiation survey meter, and it was washed repeatedly until the radioactivity was nearly constant.

The membrane after washing was covered with a film wrap, covered with an X-ray film (BioMax® MS; Kodak®)

in a darkroom, and then put in an autoradiography cassette. After being exposed for 1 week at 4° C., the X-ray film was developed. Specific signals of 2.1 kb originating in the CAG-hMMP2 expression construct were detected by autoradiography, and mice showing specific signals after hybridization with the [$^{32}$P]-labeled probe were identified as hMMP2 TG mouse founder individuals. The signal intensity of each individual was compared to the signal intensity of the positive control DNA, to estimate the number of copies of the CAG-hMMP2 expression construct introduced into the genome.

Figure 7:
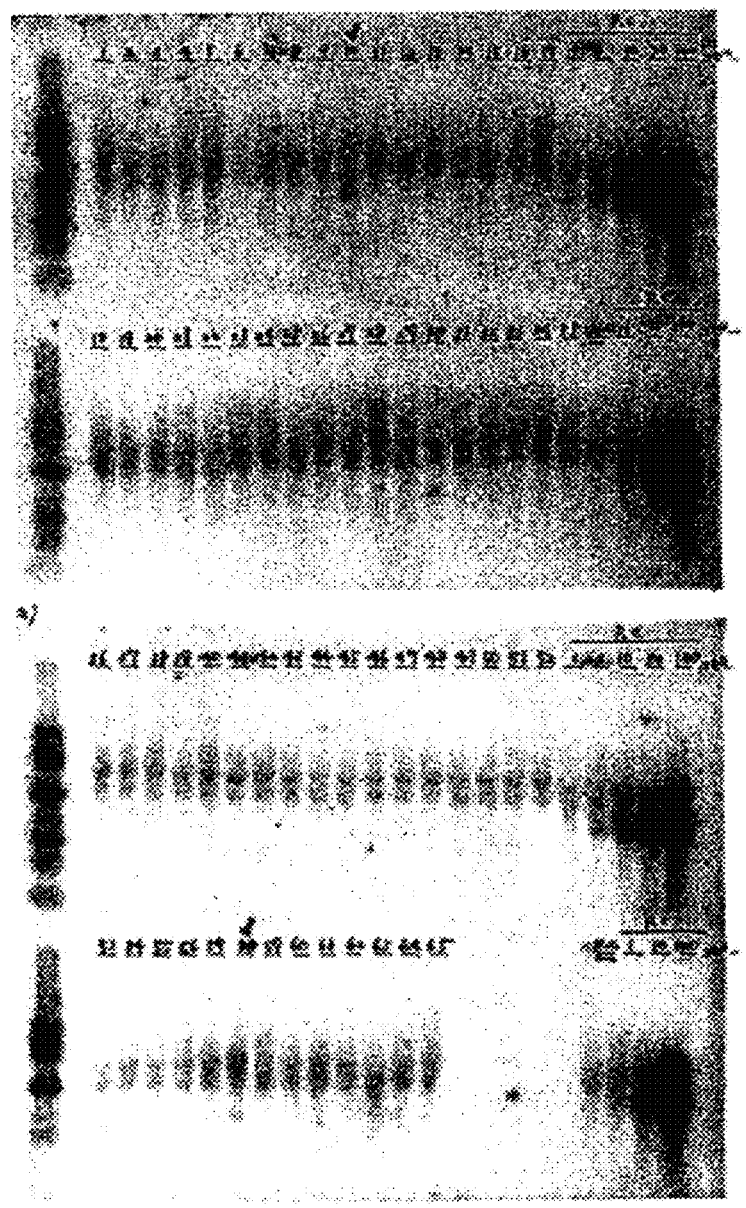
FIG. 7 shows results of a Southern hybridization using a [$^{32}$P]-labeled probe that was carried out to detect specific signals of the CAG-hMMP2 expression construct.

As shown in FIG. 7, specific signals originating in the expression construct could be detected from the fragments of the CAG-hMMP2 expression constructs which are all positive controls, by hybridization using the [$^{32}$P]-labeled probe. Since the hybridization signals originating in the expression constructs could be detected from all positive controls, the Southern analysis using the [$^{32}$P]-labeled probe indicated that the expression constructs having one or more copies introduced into the host genome could be detected.

Figure 8:
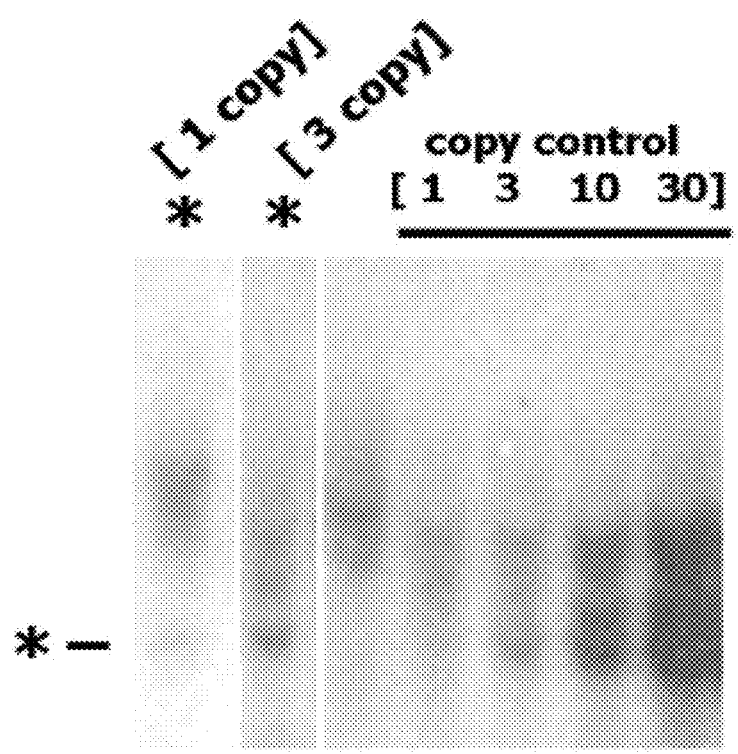
FIG. 8 shows the results of a Southern hybridization performed using tail tissue DNA from founder individuals of hMMP2-expressing TG mice; the signal intensities of the control signals were compared with known numbers of copies.

Further, as shown in FIG. 8, transgenes were confirmed in 2 mice (3%) of 65 founder candidate individuals by Southern blotting using tail DNA. The numbers of copies of the expression constructs introduced into these transgenic mouse founders were 1 to 3 copies.

<hMMP2 Expression in Various Tissues of an hMMP2-Expressing TG Mouse>

RNA was purified from various tissues of mice by TRIzol® reagent (Invitrogen®) in accordance with the accompanying instruction manual. The RNA samples were reverse-transcribed using oligo dT by SuperScript® (Invitrogen) to obtain DNA. Using a PTC-100 thermal controller (MJ Research), a PCR reaction was carried out for 28 cycles (for GAPDH) or 38 cycles (for human MMP2 and mouse Mmp2), each cycle including 10 seconds at 94° C., 20 seconds at 60° C. and 40 seconds at 72° C., and finally an extension reaction was carried out at 72° C. for 5 minutes. A control reaction was carried out for the RNA samples that were not reverse-transcribed. The primers used for amplification of GAPDH, mouse Mmp2 and human MMP2 gene were as follows. For mGAPDH, 5'-CCCTTATTGACCT-CAACTACATGGT-3' (SEQ ID NO: 1) as a sense primer and 5'-GAGGGGCCATCCACAGTCTTCTG-3' (SEQ ID NO: 2) as an antisense primer were used, for mMmp2, 5-CACCACCGAGGACTATGACC-3' (SEQ ID NO: 3) as a sense primer and 5'-TGTTGCCCAGGAAAGTGAAG-3' (SEQ ID NO: 4) as an antisense primer were used, and for hMMP2, 5'-TACTGGATCTACTCAGCCAGCAC-3' (SEQ ID NO: 5) as a sense primer and 5'-CAGGATCCATTTTCT-TCTTCACC-3' (SEQ ID NO: 6) as an antisense primer were used.

Figure 9:
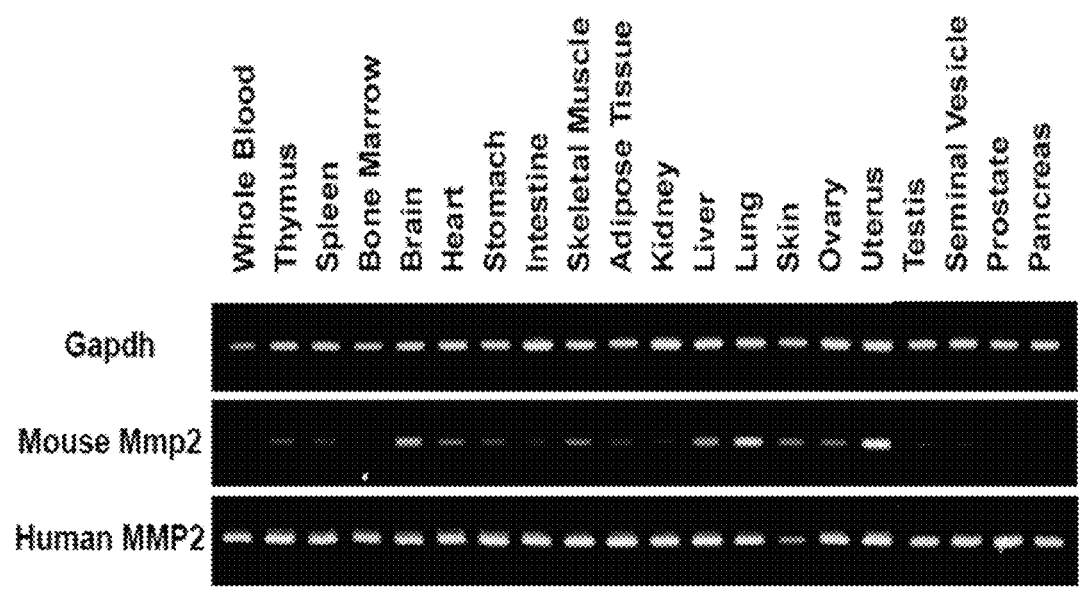
FIG. 9 shows the expression of the newly inserted hMMP2 gene and that of the endogenous mouse Mmp2 gene in various tissues extracted from an hMMP2-expressing TG mouse and evaluated by RT-PCR.

FIG. 9 shows the expression of the exogenous hMMP2 gene and the endogenous mouse Mmp2 gene as evaluated by RT-PCR in various tissues of the hMMP2-expressing TG mouse (whole blood, thymus, spleen, bone marrow, brain, heart, stomach, intestine, skeletal muscle, adipose tissue, kidney, liver, lung, skin, ovary, uterus, testis, seminal vesicle, prostate and pancreas). GAPDH was used as a positive control. Although the expression of the endogenous mouse Mmp2 was observed in a lot of tissues, there were wide differences in the expression levels among the tissues. Also, there were tissues (whole blood, bone marrow, seminal vesicle, prostate and pancreas) in which no band of the mouse Mmp2 was confirmed. On the other hand, the hMMP2 showed a high level of expression in all evaluated tissues.

Figure 10:
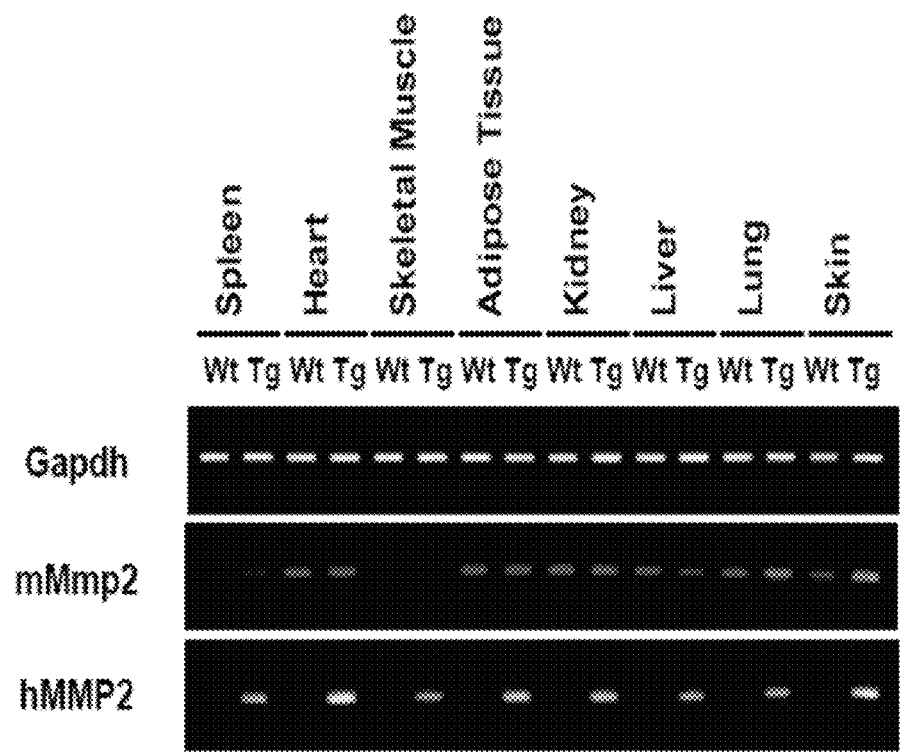
FIG. 10 shows the expression of the newly inserted hMMP2 gene and the endogenous mouse Mmp2 gene in various tissues extracted from an hMMP2-expressing TG mouse and a wild-type mouse and evaluated by RT-PCR.

FIG. 10 shows the expression of the hMMP2 gene and the mMmp2 gene as evaluated by RT-PCR in various tissues (spleen, heart, skeletal muscle, adipose tissue, kidney, liver, lung, skin) of the hMMP2-expressing TG mouse and a wild-type mouse. Expression of the hMMP2 gene was observed in all tissues of the TG mouse, but it was not observed in the wild-type mouse. There was no difference in expression of the mMmp2 gene between the tissues of the TG mouse and the wild-type mouse. In FIGS. 9 and 10, mMmp2 and Mouse Mmp2 are used as symbols that indicate the same thing.

<Observations by Computed Tomography>

Figure 11:
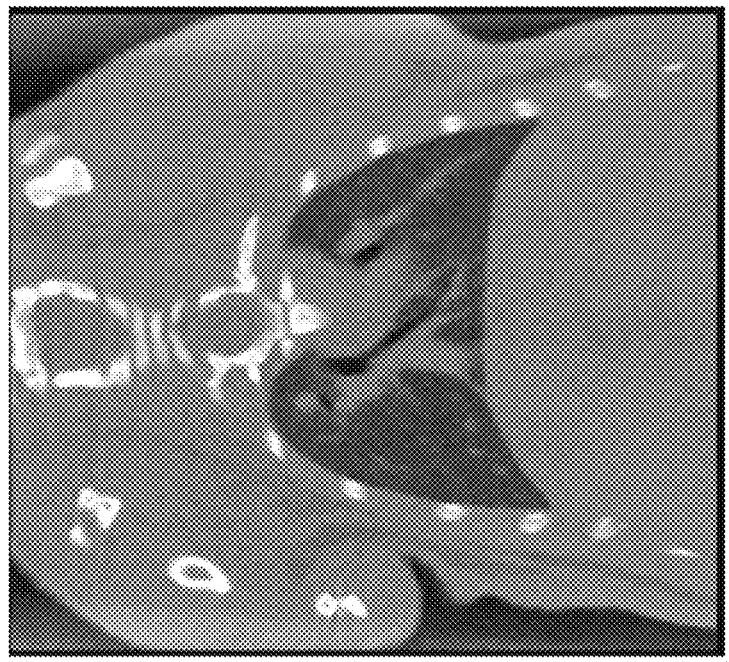
FIG. 11 shows CT images of a normal lung of a wild-type mouse.
Figure 11:
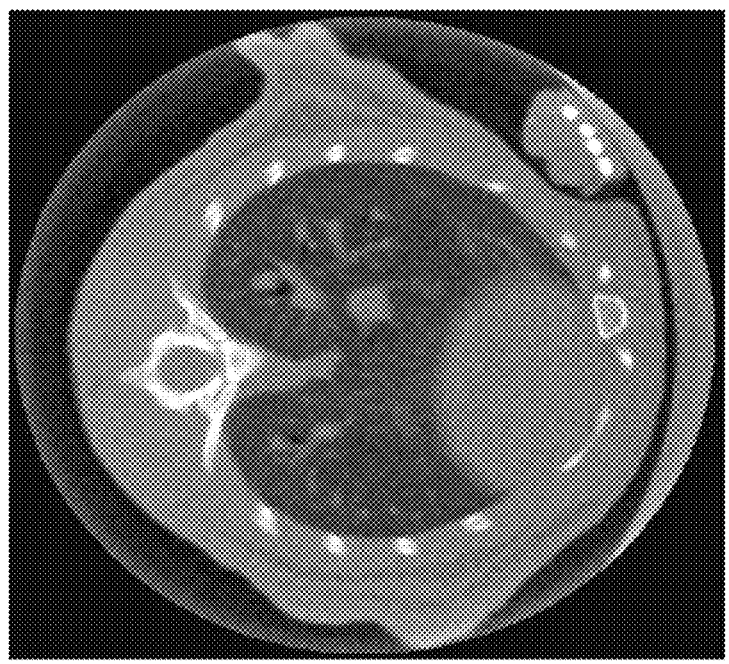
Figure 12:
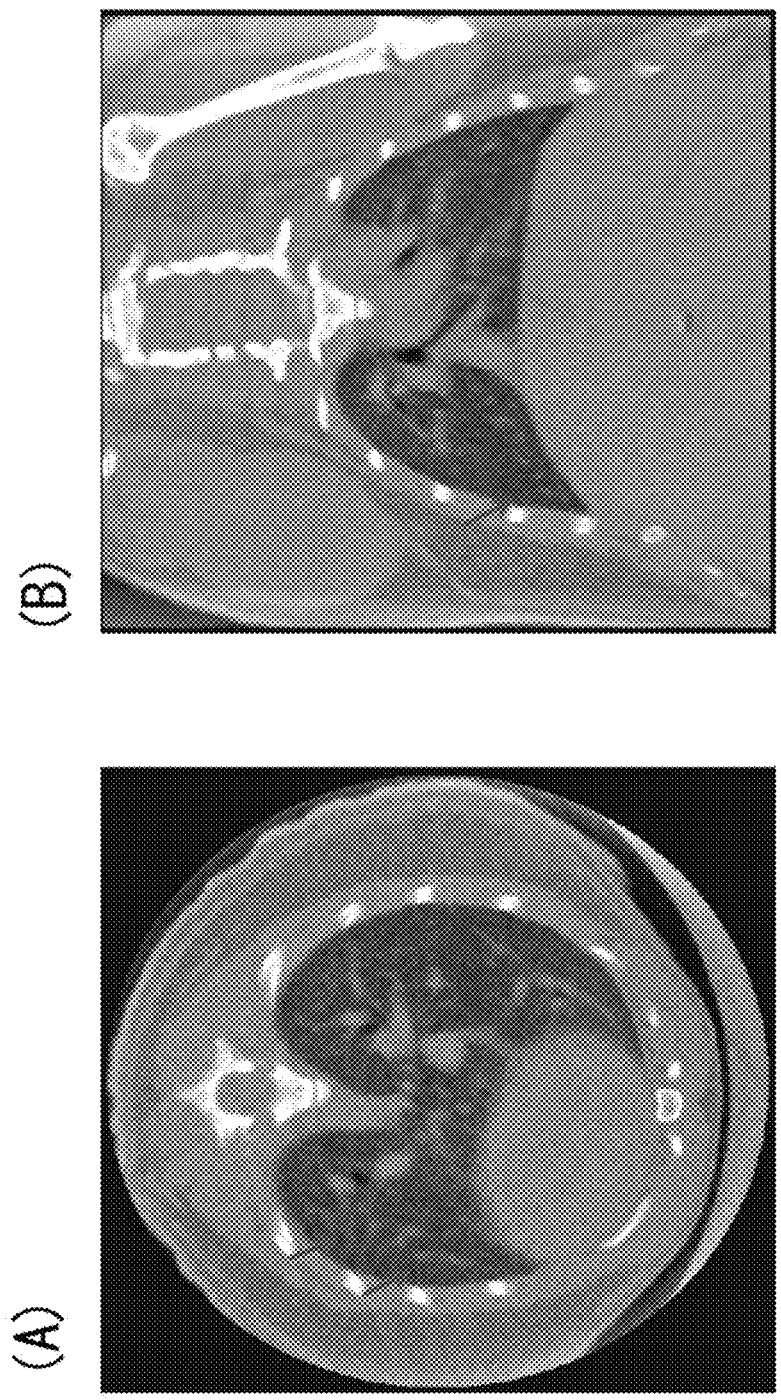
FIGS. 12(A) and (B) show CT images of the lung of an hMMP2-expressing TG mouse. Low attenuation areas indicated by arrows show the presence of emphysema.

The lungs of a wild-type mouse and an hMMP2-expressing TG mouse were observed by computed tomography (CT). FIG. 11 shows a CT image of a normal lung of the wild-type mouse. FIG. 12 shows a CT image of a lung of the hMMP2-expressing TG mouse. The low attenuation fields (regions indicated by arrows) indicate emphysema.

<Severe Inflammation Changes and Chronic Obstructive Pulmonary Disease in hMMP2-Expressing TG Mouse After Inhalation of Cigarette Smoke Extract> hMMP2-expressing TG mice were subjected to inhalation of cigarette (tobacco) smoke extract and saline, and then leukocyte numbers in the bronchoalveolar lavage fluid (BALF) were counted.

Figure 13:
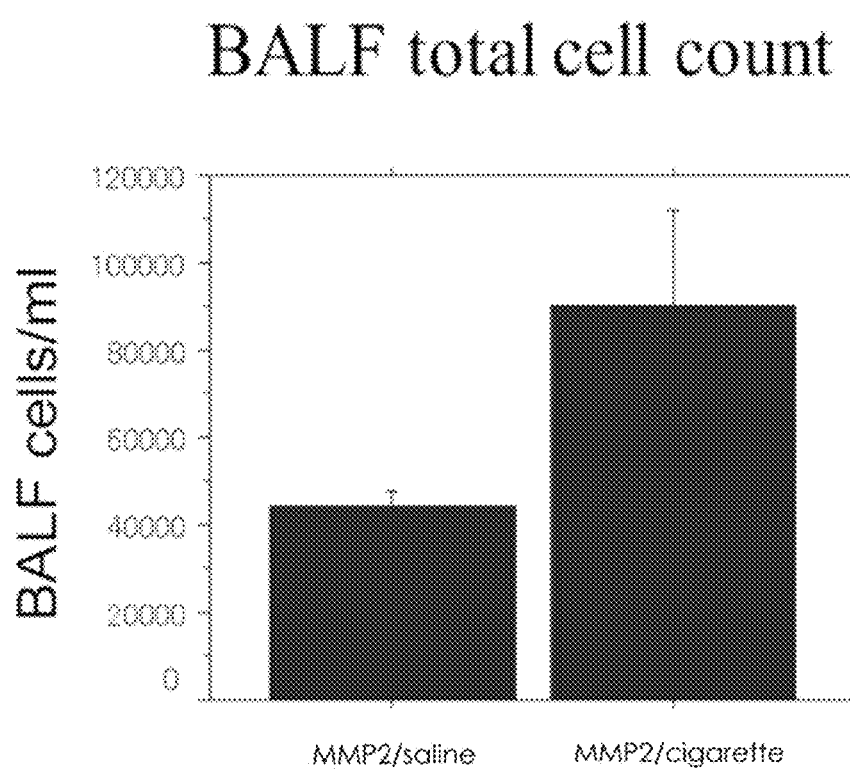
FIG. 13 shows the number of leukocytes in bronchoalveolar lavage fluid (BALF) in a mouse that inhaled saline and in an hMMP2-expressing TG mouse that inhaled a cigarette smoke extract.

As shown in FIG. 13, the hMMP2-expressing TG mouse that inhaled cigarette smoke extract (MMP2/cigarette) showed an increased number of leukocytes in BALF as compared to the hMMP2-expressing TG mouse that inhaled saline (MMP2/saline). From this, it was shown that inflammation was exacerbated in the TG mouse.

<Histological Findings of the Lungs>

The histological findings of the lungs of a wild-type mouse and an hMMP2-expressing TG mouse that inhaled cigarette smoke extract were evaluated. The lung tissues of the respective mice were stained with hematoxilin/eosin, and were observed under microscope.

Figure 14:
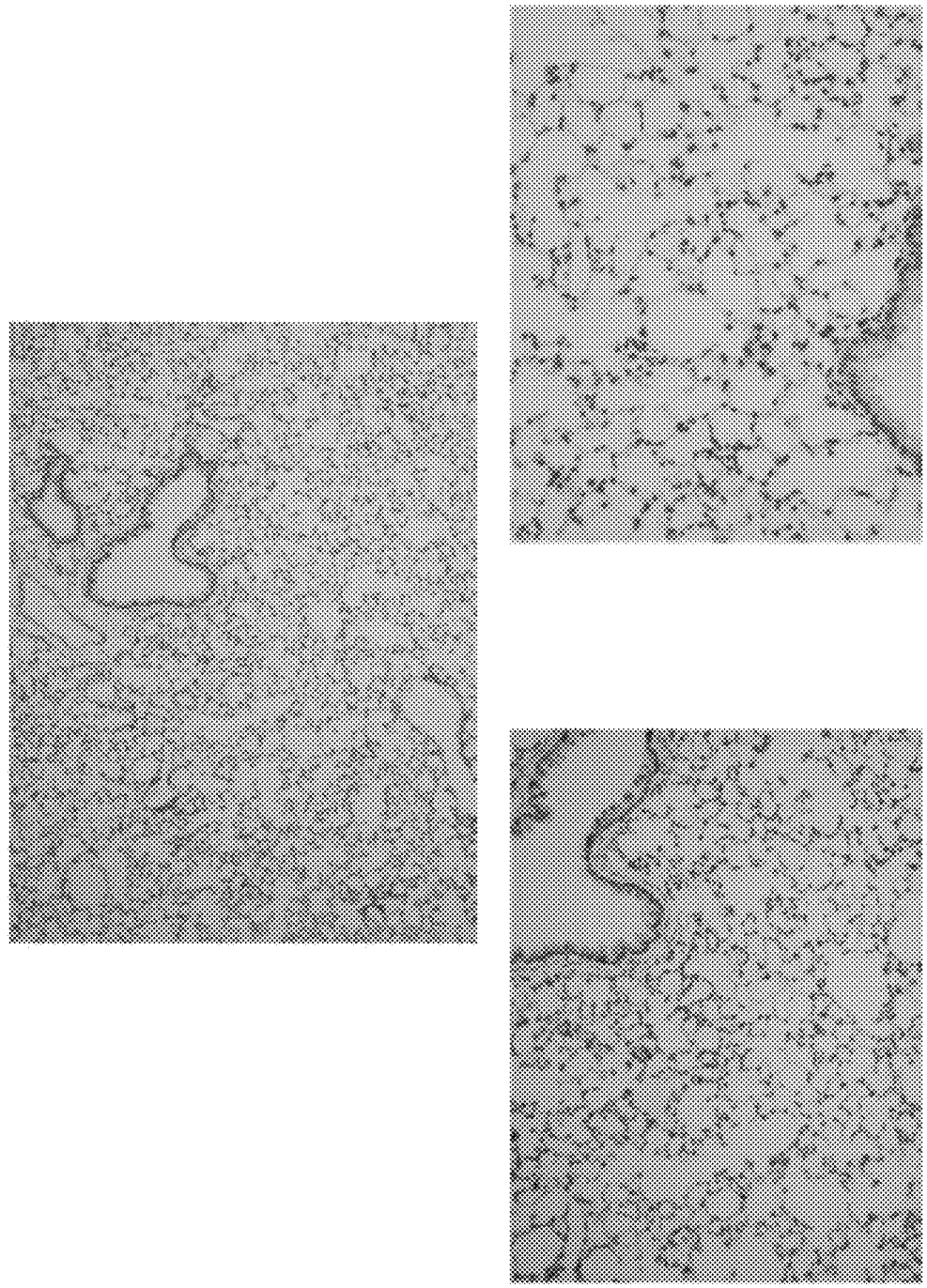
FIG. 14 shows three microphotographs of a wild-type mouse normal lung after staining.
Figure 15:
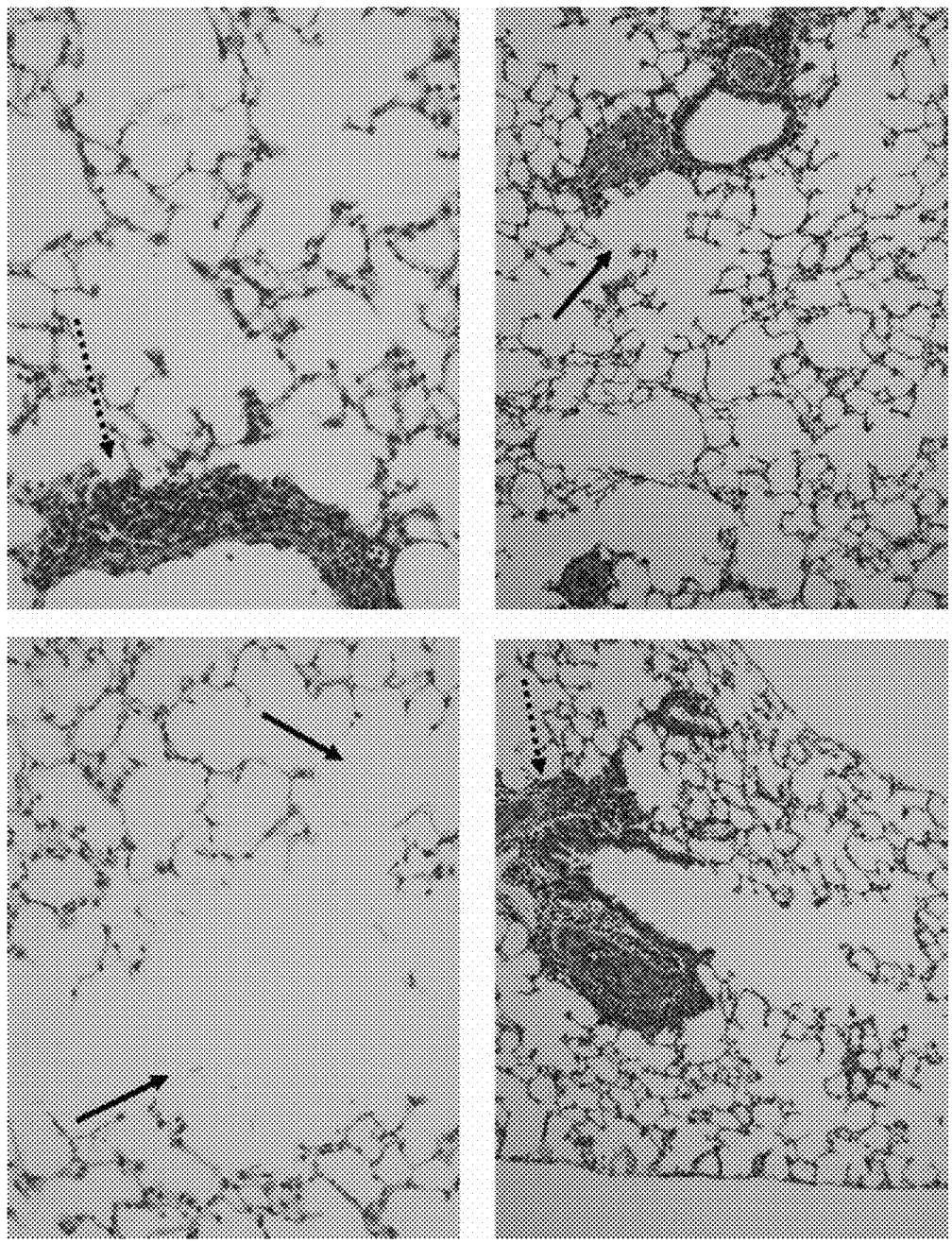
FIG. 15 shows four microphotographs of the lung from an hMMP2-expressing TG mouse after inhalation of a cigarette smoke extract.

FIG. 14 shows microphotographs of a normal lung in the wild-type mouse. FIG. 15 shows the hMMP2-expressing TG mouse lung after inhalation of cigarette smoke extract. In the hMMP2-expressing TG mouse lung, exacerbation of chronic obstructive pulmonary disease (COPD) was observed (solid arrows), and infiltration of leukocytes was increased around the blood vessels and the bronchus (dashed arrows).

<Inhibitory Effect of NFκB siRNA in COPD Using hMMP2 Expression TG Mice>

Development of COPD requires production of inflammatory cells and inflammatory cytokines such as TNF-α, IL-1β and IL-6 that result from activation of lung tissue constituent cells; the pathway of phosphatidylinositol-3-kinase (PI3)-protein kinase C-nuclear factor-κB (NFκB) plays an important role. Thus, we focused on the intracellular signaling mechanism of the NFκB pathway, and the effect of inhalation of NFκB siRNA on the development of COPD was studied.

1. Test Method

Mice were divided into 5 groups and set as follows. That is, they were divided into an (A) group, in which the wild mice were subjected to saline inhalation (wild-type mice+saline; n=6), a (B) group, in which the hMMP2-expressing TG mice were subjected to saline inhalation (MMP-2 mice+saline; n=5), a (C) group, in which the wild-type mice were subjected to inhalation of cigarette (tobacco) smoke extract (wild-type mice+cigarette smoke extract; n=10), a (D) group, in which the hMMP2-expressing TG mice were subjected to inhalation of cigarette smoke extract (MMP-2 mice+cigarette smoke extract; n=10), and an (E) group, in which the hMMP2-expressing TG mice were subjected to inhalation of cigarette smoke extract and intranasally treated with NFκβ siRNA (MMP-2 mice+cigarette smoke extract+ NFκB siRNA; n=3).

(1) Production of Smoking-Induced COPD Mouse Model

The hMMP2-expressing TG mice were exposed to cigarette smoke extract for 60 minutes every day for two weeks to produce an emphysema model. As a control, C57BL/6 wild-type mice were used.

(2) Nucleic Acid Administration Method

NFκB siRNA was dissolved with distilled water and intranasally administered, prior to exposure to the cigarette smoke extract and at the 0th, 2nd, 4th, 6th, 8th, 10th and 12th day of the exposure.

(3) RT-PCR mRNA expression was studied by using the RT-PCR method. Total RNA was isolated from lung tissue by treatment with TRIzol® (Invitrogen®, Carlsbad, Calif.). Single-strand cDNA was synthesized using reverse transcriptase (Invitrogen®) and oligo (dT). For amplification of the desired cDNA, the reaction was carried out, using AB Applied Biosystems® 7600 and AmpliTaq Gold® (AB Applied Biosystems®, Foster City, Calif.) and a primer specific to the desired cDNA, in a reaction solution at 94° C. for 10 minutes, and then followed by an optimal number of cycles, each cycle including 30 seconds at 94° C., 30 seconds at 55° C. and 30 seconds at 72° C. After 2% agarose electrophoresis, the PCR product was stained with ethidium bromide. Density analysis was carried out by using an NIH imaging system, the expression level of glyceraldehyde-3-phosphate dehydrogenase (GAPDH) was set as a standard, and expression of mRNAs of cytokines and other factors was studied and compared.

(4) Measurement and Biochemical Examination of the Cell Number

The total cell number in the bronchoalveolar lavage fluid (BALF) was measured using a ChemoMetec® (Allerod, Denmark) NUCLEOCOUNTER®.

(5) The Data were Statistically Investigated by Using ANOVA.

2. Test Results

Figure 16:
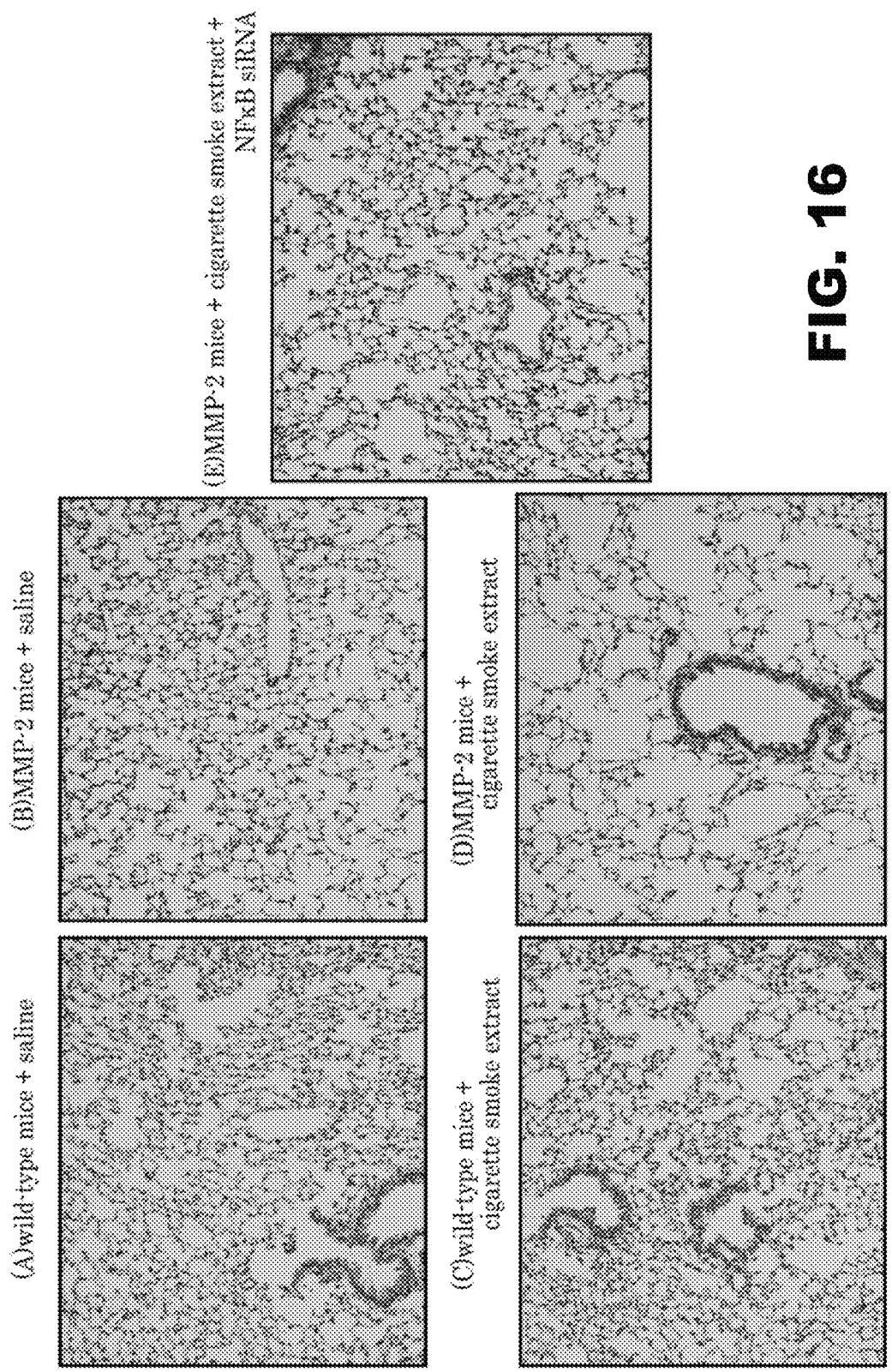
FIG. 16 contains five microphotographs of lungs showing the inhibitory effects of NFκB siRNA on COPD in hMMP2-expressing TG mice.
Figure 17:
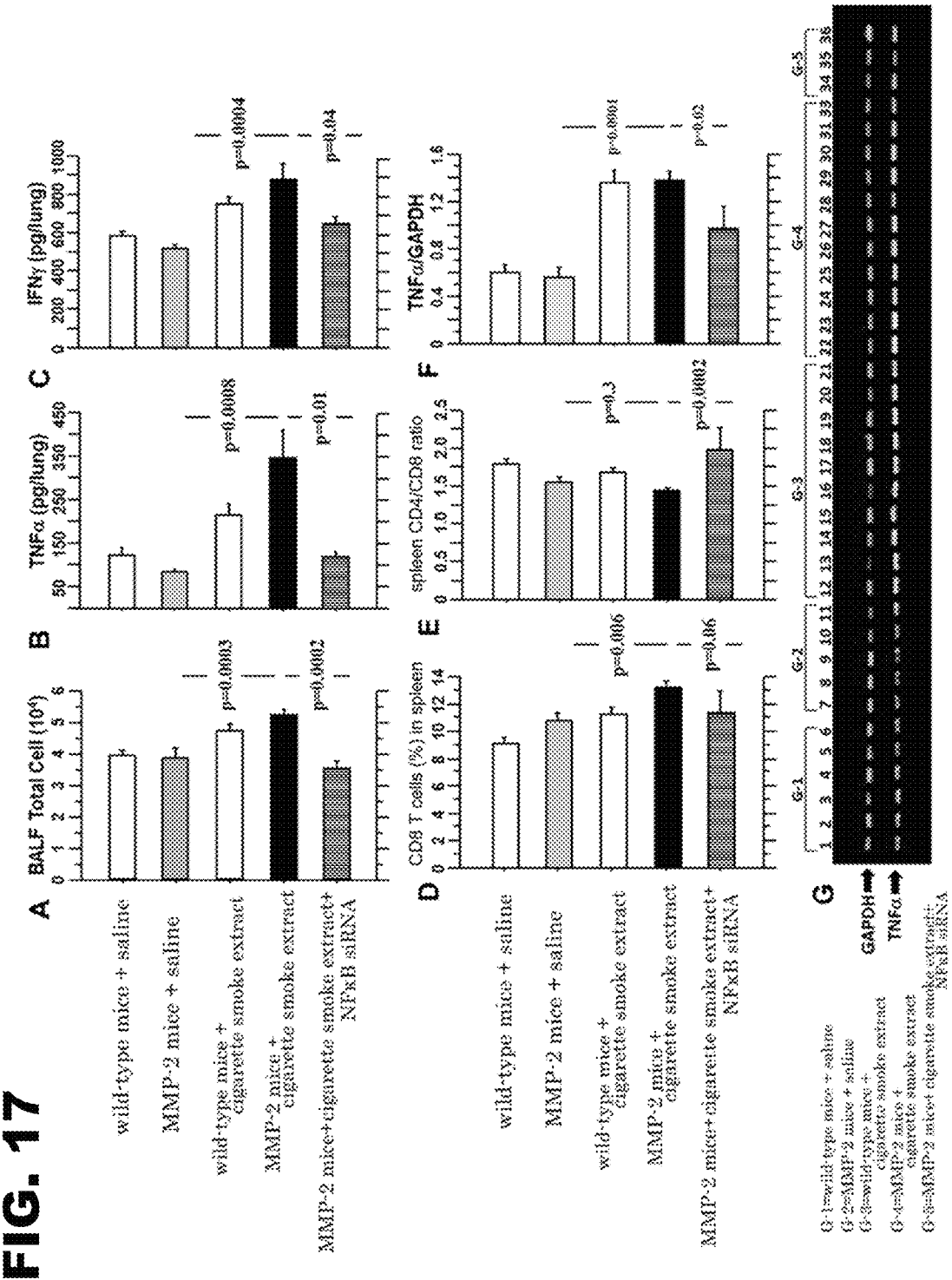
FIG. 17 contains graphs showing the results of (A) the total cell number in BALF, (B) TNFα concentration, (C) IFNγ concentration, (D) ratio of CD8 T cell number in spleen, (E) spleen CD4/CD8 ratio and (F) TNF α/GAPDH ratio, and a photograph (G) showing the expression of TNF α in samples extracted from each group.

The results are shown in FIG. 16 and FIG. 17.

As shown in FIG. 17, in the group in which the cigarette smoke extract was administered to the hMMP2-expressing TG mice (MMP-2 mice+cigarette smoke extract), the total cell number in BALF, TNF α, IFN γ and spleen CD8T cells were significantly increased as compared to the non-administered group of the hMMP2-expressing TG mice (MMP-2 mice+saline) and the group in which the cigarette smoke extract was administered to the wild-type mice (wild-type mice+cigarette smoke extract). In addition, the spleen CD4/CD8 was significantly decreased. On the other hand, in the group in which the cigarette smoke extract and the NFκB siRNA were administered to the hMMP2-expressing TG mice (MMP-2 mice+cigarette smoke extract+NFκB siRNA), these values were significantly decreased, and the spleen CD4/CD8 was restored. Note that FIG. 17(F) was prepared by quantifying the densities of the respective bands in FIG. 17(G).

As shown in FIG. 16, when comparing the control group ((C) wild-type mice+cigarette smoke extract) and the group in which the cigarette smoke extract was administered to the hMMP2-expressing TG mice ((D) MMP-2 mice+cigarette smoke extract) that showed the same mRNA expression level of TNFα associated with inflammation in FIG. 17(F), the group in which the cigarette smoke extract was administered to the hMMP2-expressing TG mice ((D) MMP-2 mice+cigarette smoke extract) showed large-scale destruction of the alveolar wall, indicating significant exacerbation of COPD. On the other hand, as compared to the group in which the cigarette smoke extract was administered to the hMMP2-expressing TG mouse ((D) MMP-2 mice+cigarette smoke extract), the group in which the cigarette smoke extract and NFκB siRNA were administered to the hMMP2-expressing TG mouse ((E) MMP-2 mice+cigarette smoke extract+NFκB siRNA) showed reduced destruction of the alveolar wall, indicating that changes in emphysema and COPD were significantly decreased.

As described above, the hMMP2-expressing TG mouse group was found to have high incidents of COPD caused by inhalation of cigarette smoke extract.

<Effect of Bleomycin on hMMP2-Expressing TG Mice>

Saline or bleomycin was administered to hMMP2-expressing TG mice by using an osmotic pump to investigate the effect of bleomycin. As test groups, two groups, a group receiving saline (MMP-2 mice+saline, n=4) and a group receiving bleomycin (MMP-2 mice+bleomycin, n=4), were used.

In order to administer bleomycin, pentobarbital was intraperitoneally injected into the hMMP2-expressing TG mouse (female, 8 weeks old), and then an ALZET® osmotic pump was subcutaneously implanted in the back of the mouse. 200 μL of bleomycin or a saline aqueous solution was pre-injected into the ALZET osmotic pump.

On the 21st day after the implantation of the osmotic pumps, pentobarbital was intraperitoneally administered to the mouse, the neck skin and the muscle of the mouse were stripped under anesthesia to expose the trachea. Saline was injected into the trachea using an indwelling needle to collect the bronchoalveolar lavage fluid (BALF). Subsequently, the thorax was opened, perfused with saline, and the lung tissue was excised.

mRNA expression was studied by using the RT-PCR method. Total RNA was isolated from a lung tissue by treatment with TRIzol® (Invitrogen®, Carlsbad, Calif.). Single-strand cDNA was synthesized using reverse transcriptase (Invitrogen®) and oligo (dT). For amplification of the desired cDNA, the reaction was carried out, using AB Applied Biosystems® 7600 and AmpliTaq Gold® (AB Applied Biosystems®, Foster City, Calif.) and a primer specific to the desired cDNA, in a reaction solution at 94° C. for 10 minutes, and then followed by an optimal number of cycles, each cycle including 30 seconds at 94° C., 30 seconds at 55° C. and 30 seconds at 72° C. After 2% agarose electrophoresis, the PCR product was stained with ethidium bromide. Density analysis was carried out by using an NIH imaging system, the expression level of glyceraldehyde-3-phosphate dehydrogenase (GAPDH) was set as a standard, and expression of mRNAs of cytokines and other factors was studied and compared.

The total cell number in the bronchoalveolar lavage fluid was measured using a ChemoMetec® (Allerod, Denmark) NUCLEOCOUNTER®. The total protein amount in the bronchoalveolar lavage fluid was measured by a dye-binding assay (Bio-Rad® Laboratories, Hercules, Calif.). Furthermore, the data were statistically evaluated by using ANOVA.

Figure 18:
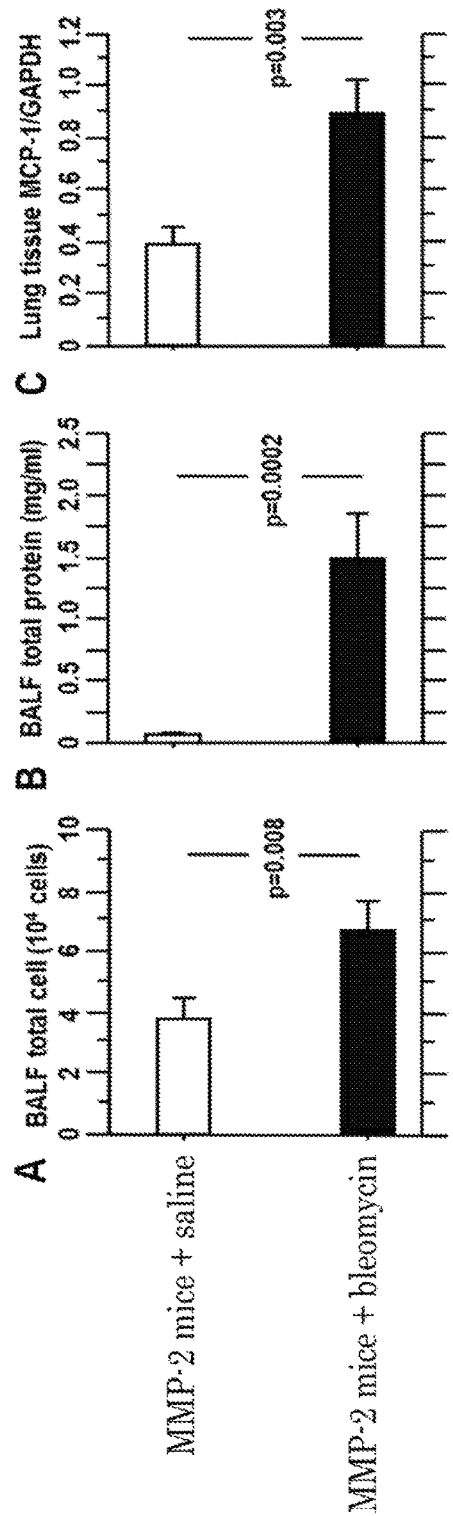
FIG. 18 shows the results obtained after infusion of bleomycin in hMMP2-expressing TG mice.
Figure 18:
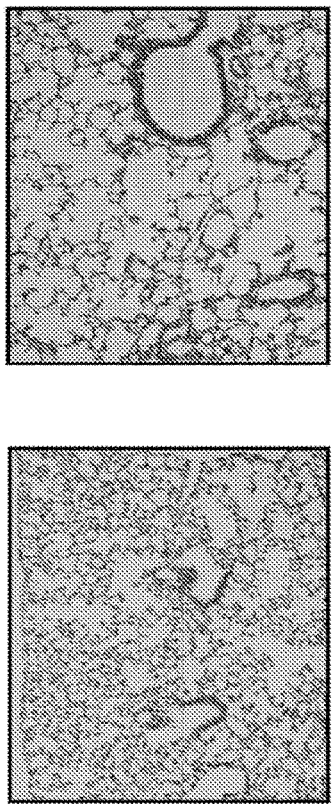

The results are shown in FIG. 18. The group receiving bleomycin (MMP-2 mice+bleomycin) showed significantly high values in the total cell number in BALF (A), the total protein level in BALF (B) and the monocyte chemoattractant protein-1 in the lung tissue (MCP-1) (C) as compared to the control group receiving saline (MMP-2 mice+saline). In addition, the group receiving bleomycin showed significantly high emphysematous changes (D) as compared to the control group.

As mentioned above, the hMMP2-expressing TG mouse group had large-scale destruction of the alveolar wall after administration of bleomycin, indicating high incidents of COPD.

<Effects of Ovalbumin on hMMP2-Expressing TG Mice> hMMP2-expressing TG mice were sensitized with ovalbumin by intraperitoneal administration, then subjected to ovalbumin inhalation through a nebulizer for 5 days to produce asthma models. Control mice were given saline. As test groups, two groups, a group receiving saline (MMP-2 mice+saline, n=3) and a group receiving ovalbumin by intraperitoneal and inhalation administrations (MMP-2 Mice+ovalbumin, n=3), were used.

On the 0th, 7th, 14th and 21st day from the start of the test, 10 μg of ovalbumin and 1 mg of Al(OH)$_3$, or alternatively saline, were intraperitoneally administered, and then on the 28th, 29th, 30th, 31st and 32nd day, the mice were subjected to inhalation of 2% ovalbumin or saline. On the 33rd day from the start of the test, pentobarbital was intraperitoneally administered to the mice, the neck skin and the muscle of the mouse were stripped under anesthesia to expose the trachea. Saline was injected into the trachea using an indwelling needle to collect the bronchoalveolar lavage fluid (BALF). Subsequently, the thorax was opened, perfused with saline, and the lung tissue was excised.

mRNA expression was studied by RT-PCR. Total RNA was isolated from the lung tissue by treatment with TRIzol® (Invitrogen®, Carlsbad, Calif.). Single-strand cDNA was synthesized using reverse transcriptase (Invitrogen®) and oligo (dT). For amplification of the desired cDNA, the reaction was carried out, using AB Applied Biosystems® 7600 and AmpliTaq Gold® (AB Applied Biosystems®, Foster City, Calif.) and a primer specific to the desired cDNA, in a reaction solution at 94° C. for 10 minutes, and then followed by an optimal number of cycles, each cycle including 30 seconds at 94° C., 30 seconds at 55° C. and 30 seconds at 72° C. After 2% agarose electrophoresis, the PCR product was stained with ethidium bromide. Density analysis was carried out by using an NIH imaging system, the expression level of glyceraldehyde-3-phosphate dehydrogenase (GAPDH) was set as a standard, and expression of mRNAs of cytokines and other factors was studied and compared.

The total cell number in the bronchoalveolar lavage fluid was measured using a ChemoMetec® (Allerod, Denmark) NUCLEOCOUNTER®. The total protein amount in the bronchoalveolar lavage fluid was measured by a dye-binding assay (Bio-Rad® Laboratories, Hercules, Calif.). Furthermore, the data were statistically evaluated by using ANOVA.

Figure 19:
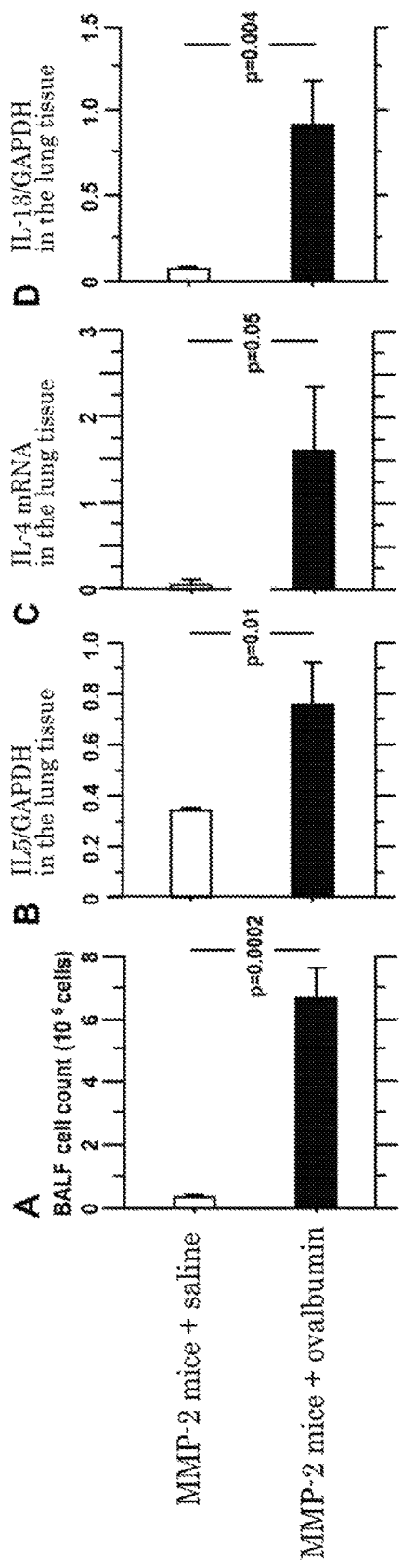
FIG. 19 shows data confirming the influence of ovalbumin on hMMP2-expressing TG mice.
Figure 19:
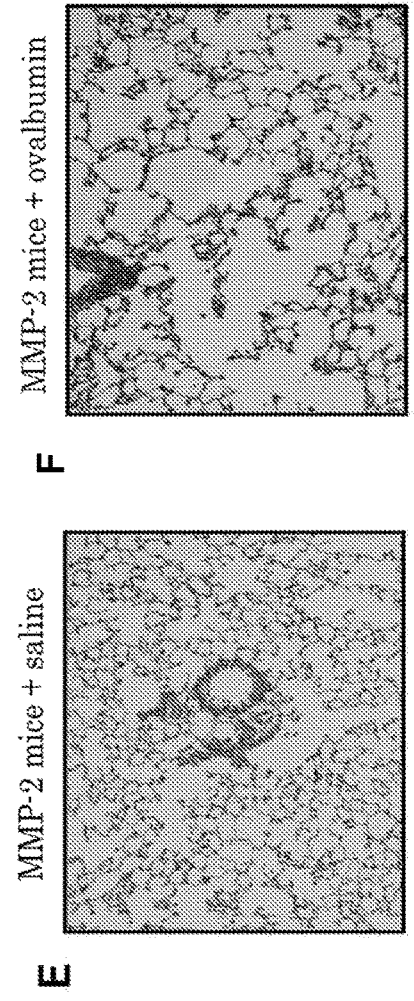

The results are shown in FIG. 19. The group sensitized with ovalbumin (MMP-2 mice+ovalbumin) had a significantly high total cell number in the bronchoalveolar lavage fluid (BALF) (A) and showed significantly high expression levels of interleukin-5 (IL5; B), interleukin-4 (IL4; C) and interleukin-13 (IL13; D) in the lung tissue as compared to the control group receiving saline (MMP-2 mice+saline). The mice sensitized with ovalbumin also showed significantly higher degrees of bronchitis and emphysema (E) as compared to the control group.

As mentioned above, the hMMP2-expressing TG mouse group had large-scale destruction of the alveolar wall after administration of ovalbumin, indicating high incidents of COPD.

As mentioned above, according to embodiments of the present teachings, TG mice that systemically express hMMP2 have been provided. Since the TG mice naturally develop COPD, research on COPD can be dramatically advanced. Note that cigarette smoke, the cigarette smoke extract or cigarette component, albumin and bleomycin were used as inducers in the embodiments. However, other inducers may include environmental pollutants, proteases, etc. Moreover, a plurality of inducers can also be used in combination. In addition, inhalation of cigarette smoke and its extract or albumin, and intraperitoneal administration of bleomycin were used as methods for inducting in the embodiments. However, other methods can be used including intravenous injection, oral administration, subcutaneous administration, transtracheal administration, etc.

The invention claimed is:

1. A transgenic (TG) mouse having a genome that comprises an early-immediate enhancer of human cytomegalovirus (CMV enhancer), a β-actin promoter and the entire cDNA of human matrix metalloproteinase 2 (hMMP2) disposed downstream of the promoter, wherein the hMMP2 is systemically expressed in the TG non-human mammal.

2. A method for producing an animal model for developing a disease selected from the group consisting of chronic obstructive pulmonary disease (COPD), pulmonary fibrosis, airway remodeling and pulmonary hypertension, the method comprising:
   administering an inducer to the TG mouse according to claim 1, wherein the inducer is cigarette smoke, a cigarette smoke extract, a cigarette component, bleomycin or albumin.

3. The TG mouse according to claim 1, wherein the CMV enhancer is upstream of the β-actin promoter.

4. A method for producing an animal model for developing a disease selected from the group consisting of chronic obstructive pulmonary disease (COPD), pulmonary fibrosis, airway remodeling and pulmonary hypertension, the method comprising:
   administering an inducer to the TG mouse according to claim 3, wherein the inducer is cigarette smoke, a cigarette smoke extract, a cigarette component, bleomycin or albumin.

5. The TG mouse according to claim 3, wherein the β-actin promoter is a chicken β-actin promoter that is operably linked to the hMMP2 via a rabbit β-globin.

6. A method for producing a transgenic (TG) mouse, comprising:
   providing an hMMP2 expression construct that includes an early-immediate enhancer of human cytomegalovirus (CMV enhancer) and the entire cDNA of human matrix metalloproteinase 2 (hMMP2) downstream of a β-actin promoter,
   introducing the hMMP2 expression construct into a fertilized egg,
   implanting said fertilized egg in a mouse and
   allowing said fertilized egg to develop in the mouse.

7. The method for producing the TG mouse according to claim 6, wherein an offspring from said fertilized egg is raised as a founder candidate individual, genomic DNA is extracted from tissues of the founder candidate individual, and the presence of the hMMP2 expression construct in the extracted genomic DNA is ascertained.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Mus musculus

<400> SEQUENCE: 1
cccttattga cctcaactac atggt                                           25

<210> SEQ ID NO 2
<211> LENGTH: 23
<212> TYPE: DNA
<213> ORGANISM: Mus musculus

<400> SEQUENCE: 2
gaggggccat ccacagtctt ctg                                             23

<210> SEQ ID NO 3
<211> LENGTH: 20
<212> TYPE: DNA
<213> ORGANISM: Mus musculus
```

```
<400> SEQUENCE: 3
caccaccgag gactatgacc                                              20

<210> SEQ ID NO 4
<211> LENGTH: 20
<212> TYPE: DNA
<213> ORGANISM: Mus musculus

<400> SEQUENCE: 4
tgttgcccag gaaagtgaag                                              20

<210> SEQ ID NO 5
<211> LENGTH: 23
<212> TYPE: DNA
<213> ORGANISM: Homo sapiens

<400> SEQUENCE: 5
tactggatct actcagccag cac                                          23

<210> SEQ ID NO 6
<211> LENGTH: 23
<212> TYPE: DNA
<213> ORGANISM: Homo sapiens

<400> SEQUENCE: 6
caggatccat tttcttcttc acc                                          23
```